United States Patent
Van Geert et al.

(10) Patent No.: US 6,983,843 B2
(45) Date of Patent: Jan. 10, 2006

(54) CONTAINER AND A CONTAINER ACCESSORY

(75) Inventors: Peter Van Geert, Kraainem (BE); Mischa Marteleur, Langdorp (BE); Johan Berte, Kersbeek-Miskom (BE)

(73) Assignee: Eli Lilly and Company, Indianapolis, IN (US)

( * ) Notice: Subject to any disclaimer, the term of this patent is extended or adjusted under 35 U.S.C. 154(b) by 12 days.

(21) Appl. No.: 10/433,399

(22) PCT Filed: Nov. 21, 2001

(86) PCT No.: PCT/US01/43132

§ 371 (c)(1),
(2), (4) Date: Dec. 8, 2003

(87) PCT Pub. No.: WO02/064438

PCT Pub. Date: Aug. 22, 2002

(65) Prior Publication Data

US 2004/0129596 A1    Jul. 8, 2004

(30) Foreign Application Priority Data

Dec. 6, 2000 (GB) .................................. 0029752
Aug. 10, 2001 (GB) .................................. 0119484
Aug. 28, 2001 (GB) .................................. 0120767

(51) Int. Cl.
*B65D 21/00* (2006.01)
*B65D 23/08* (2006.01)
(52) U.S. Cl. ................. 206/438; 206/446; 206/521; 215/12.1
(58) Field of Classification Search ............ 206/438, 206/570, 446, 521; 215/12.1, 13.1, DIG. 3; 220/23.83, 670, 671
See application file for complete search history.

(56) References Cited

U.S. PATENT DOCUMENTS

| 1,063,351 | A | * | 6/1913 | Hyatt | 215/12.1 |
| 2,135,236 | A | * | 11/1938 | Koppelman | 215/12.1 |
| 3,613,761 | A | * | 10/1971 | Moody | 215/12.1 |
| 3,977,555 | A | | 8/1976 | Larson | |
| 3,993,063 | A | | 11/1976 | Larrabee | |

(Continued)

FOREIGN PATENT DOCUMENTS

EP    0 303 781    2/1989

(Continued)

*Primary Examiner*—Jim Foster
(74) *Attorney, Agent, or Firm*—John C. Demeter

(57) ABSTRACT

The invention is particularly, although not exclusively, concerned with a protective container (1; 1') for fragile articles (100), such as bottles, vials or ampoules of fluid medicament. In one aspect, the protective container is provided with impact energy-absorbing structural features for protecting the fragile article in the event of it being dropped, for instance impact energy-absorbing collars (45, 47; 45', 47') at, or adjacent to, the forward and rear end surfaces, respectively. In other aspects of the invention, the protective container (1; 1') has a hanging member (17; 17') and/or a corrugated wall structure (37, 39, 41, 43; 37', 39'41'43') and/or a latchable flap (55; 55') for a dispensing aperture (57; 57') in the container. In yet further aspects, there is provided a protective container having a re-formable label (101; 101') and/or an internal skirt (73; 73') for locating and retaining a feature on an article to be housed therein. The invention further provides a nozzle accessory (150) for attachment to a container to enable the contents of the container to be discharged.

25 Claims, 16 Drawing Sheets

U.S. PATENT DOCUMENTS

| | | | |
|---|---|---|---|
| 4,092,546 A | 5/1978 | Larrabee | |
| 4,114,759 A | 9/1978 | Maloney | |
| 4,245,685 A | 1/1981 | Nemitz et al. | |
| 4,300,612 A * | 11/1981 | Schroeder et al. | 206/521 |
| 4,746,017 A * | 5/1988 | Howard et al. | 215/12.1 |
| 6,568,434 B2 * | 5/2003 | Zinger | 141/2 |

FOREIGN PATENT DOCUMENTS

| | | |
|---|---|---|
| GB | A-304 984 | 1/1929 |
| GB | A-412 609 | 7/1934 |
| GB | 705206 | 3/1954 |
| GB | A-1 486 892 | 9/1977 |
| GB | 2 154 562 | 9/1985 |

* cited by examiner

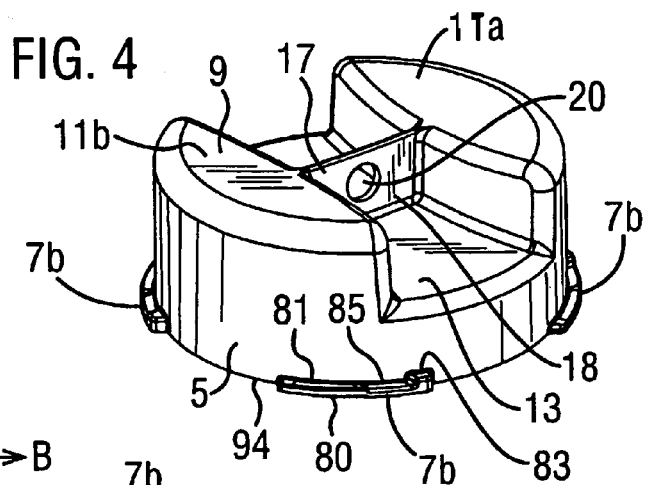
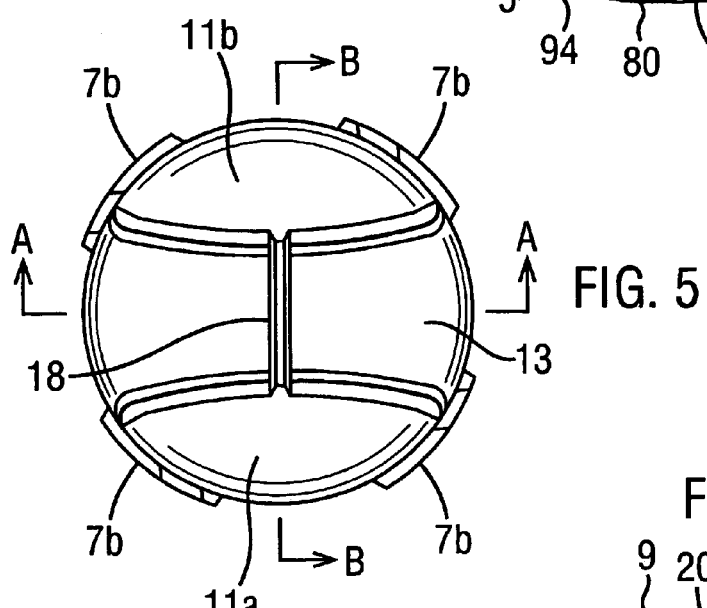
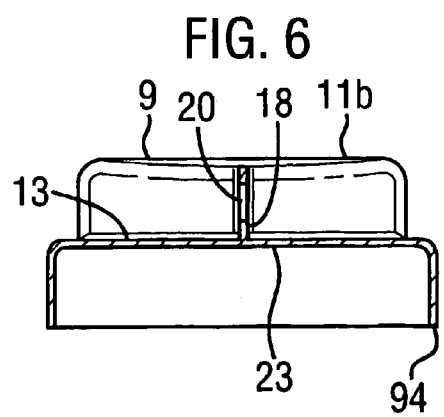
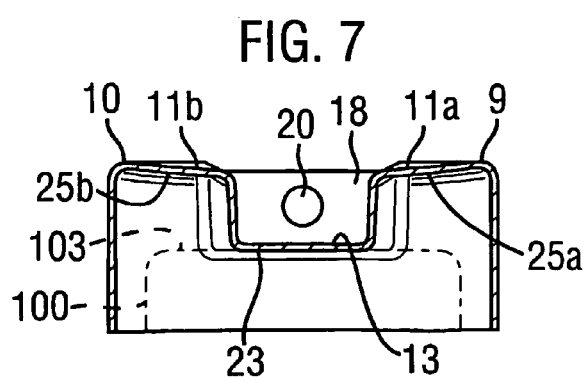

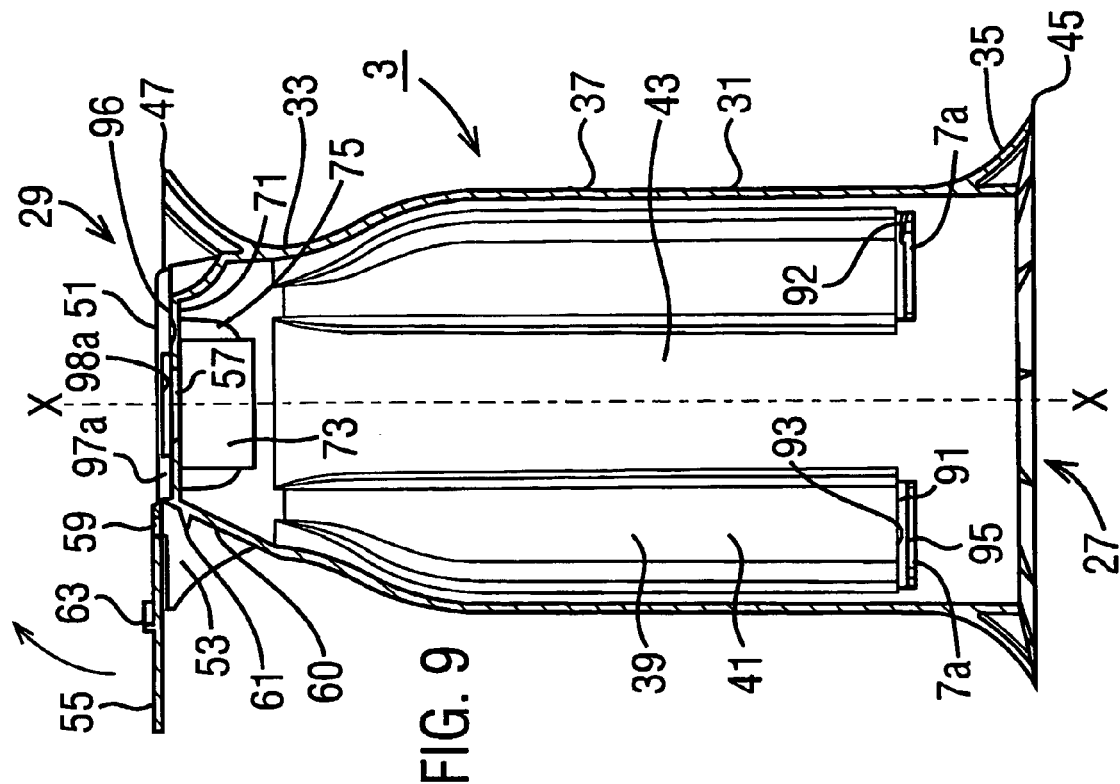
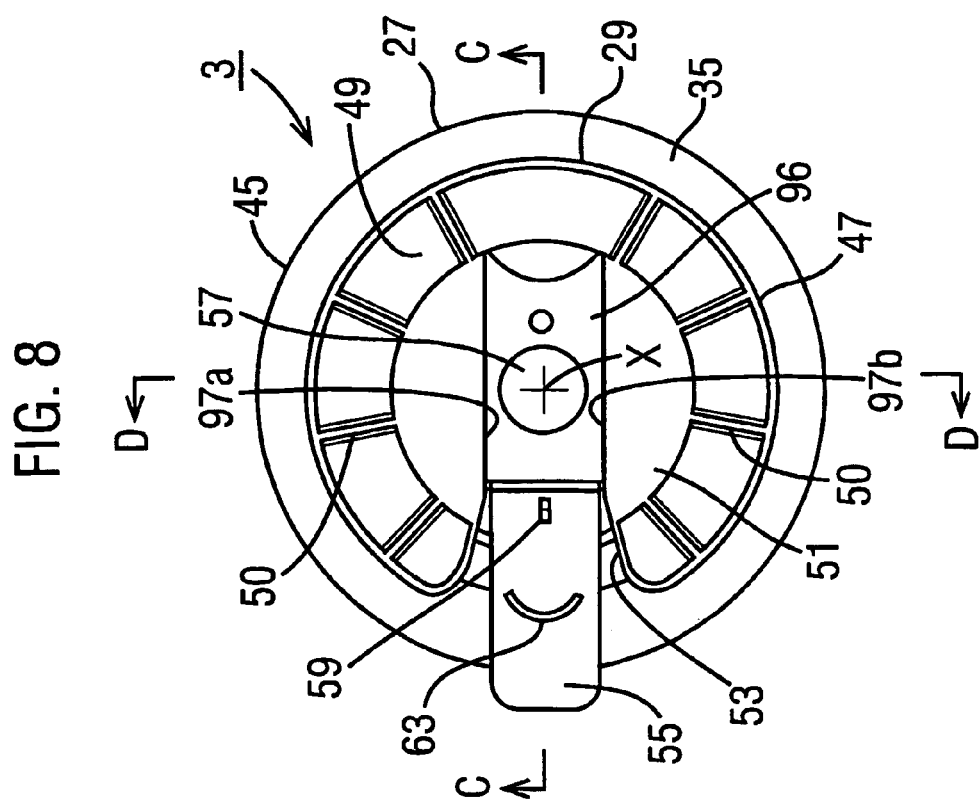

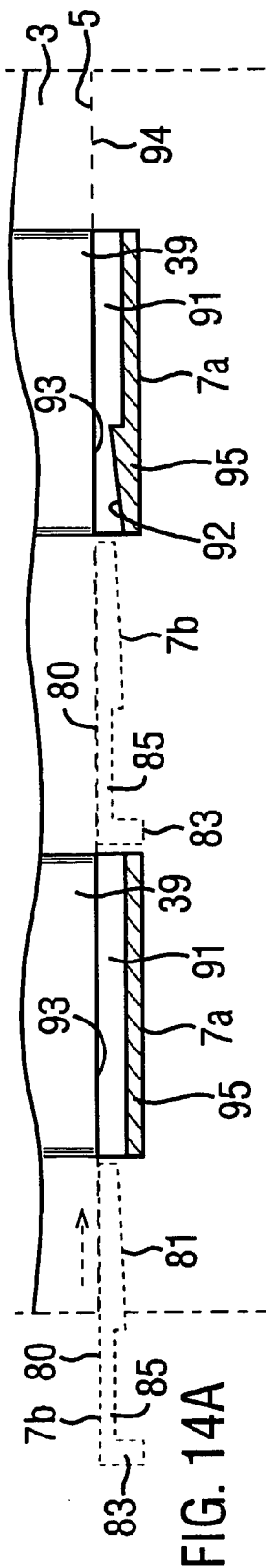
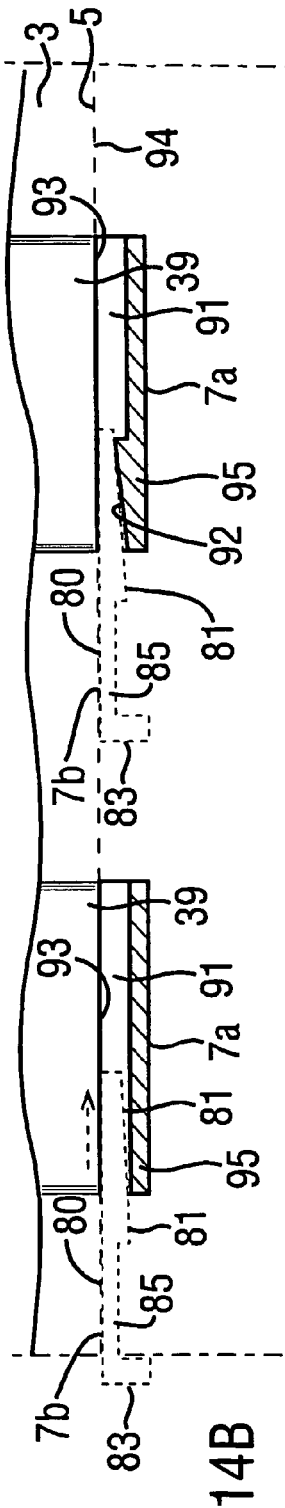
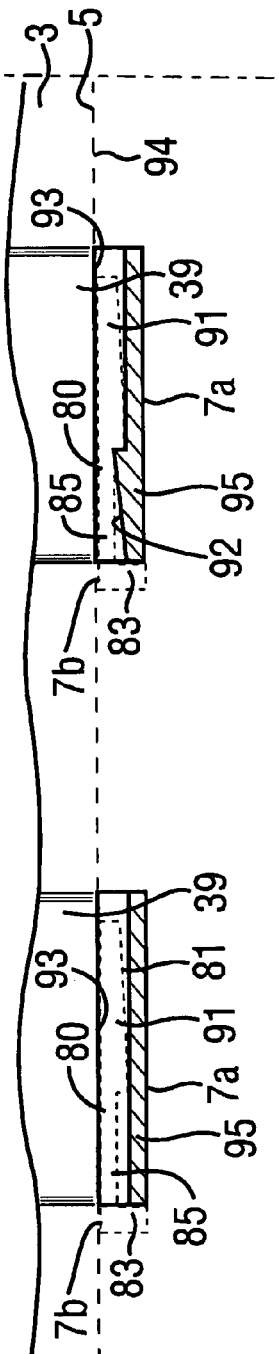
FIG. 14A
FIG. 14B
FIG. 14C

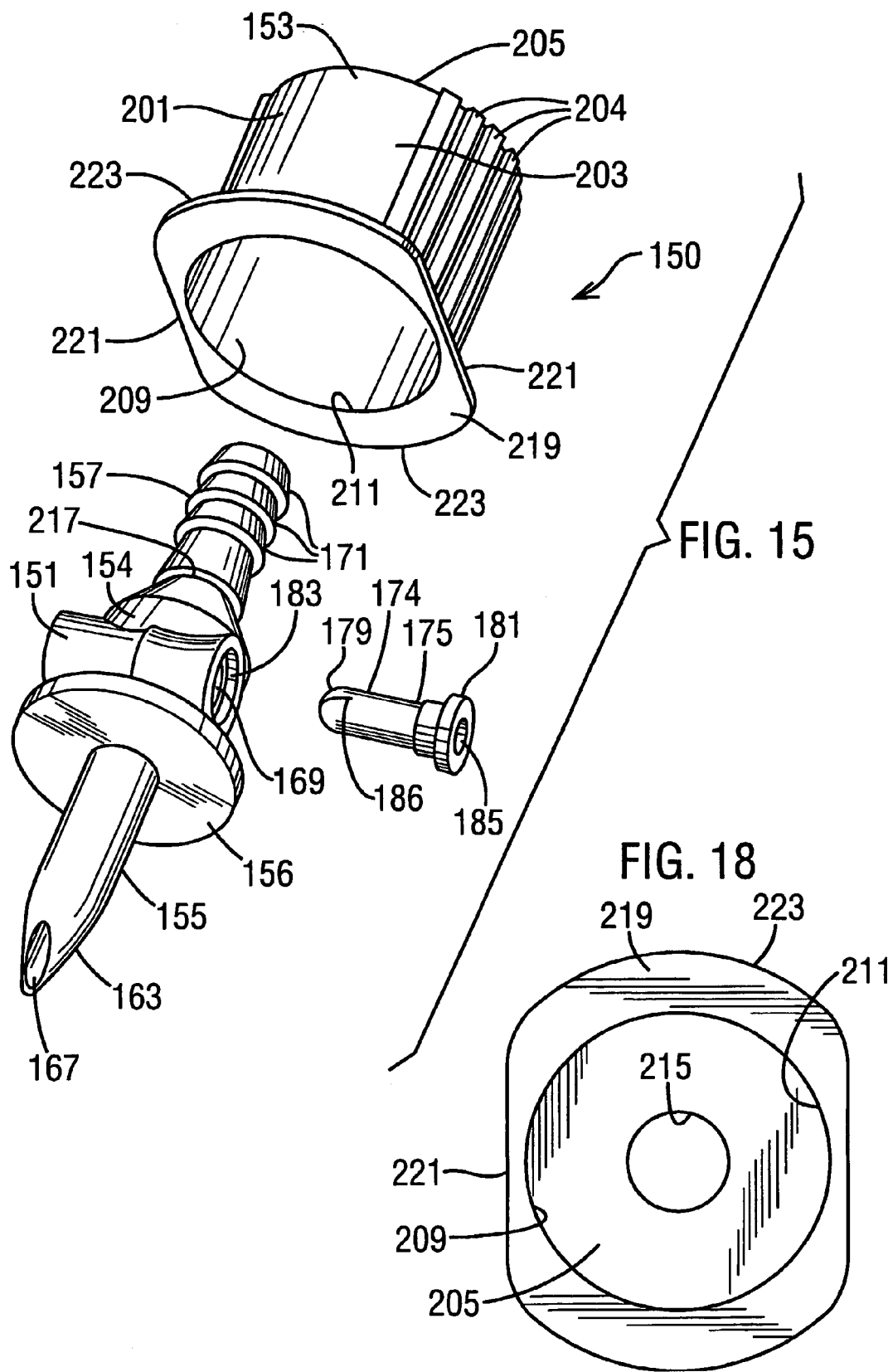

CONTAINER AND A CONTAINER ACCESSORY

FIELD OF THE INVENTION

The present invention relates to a container and is particularly, although not exclusively, concerned with a protective container to protect receptacles of fluid medicament against breakage. The present invention further relates to an accessory for a container structure.

BACKGROUND OF THE INVENTION

It is known to house fluid medicament in a receptacle (e.g. a bottle, vial or ampoule) having a piercable closure such as a rubber stopper. Such receptacles are typically made from medical grade glass which is non-reactive with the medicament. However, glass is intrinsically brittle. This means that the receptacle is likely to break if dropped. This leads to wastage of the medicament. Moreover, the medicament may be toxic and its spillage a health hazard.

To address this problem, it is known to house the receptacle in a protective container. The protective container may be constructed as an applicator through which a user holds the receptacle and accesses and dispenses the medicament, e.g. by providing the container with an aperture through which a syringe needle can be inserted through the rubber stopper of the receptacle for withdrawal of a dose of the medicament into the syringe.

While the use of a protective container resolves the problem of spillage, the protective containers in the art could be improved to provide better protection against breakage of the receptacle if the container is dropped.

As an example of a previously proposed protective container there may be mentioned the protective containers in which 250 ml glass bottles of the bovine respiratory disease antibiotic Micotil® (tilmicosin) are sold by Eli Lilly and Company Limited. The protective container is particularly needed in this instance because the glass bottle will invariably be used in conditions where there is a likelihood of it being dropped and broken, especially when trying to insert a needle into the stopper of the bottle, e.g. because the cattle are stressed and therefore difficult to handle, the medicament is being administered outdoors in adverse weather conditions and/or the medicament is being administered while riding horseback. This prior protective container has a 3-piece construction. Moreover, it is made from polycarbonate to make it transparent so that there is no need for an overlabel as the label on the bottle can be observed.

Another hitherto proposed protective container for a medicament-filled glass bottle is made known in EP-A-0 303 781. This protective safety container has a base part and a hollow, generally cylindrical body part which snap fit together to hold the bottle therein. A plurality of spaced-apart ribs extend longitudinally over the inner surface of the side of the container to space the side of the bottle from the inner surface of the container. These "spacers" act to provide air cushions circumferentially around the side of the bottle. The base has a bottom wall which is concave to provide a raised centre on which the bottom of the bottle sits and a surrounding annular air cushion. The top wall of the body part has a central depression in which is formed an aperture closed by a frangible seal. The depression results in an annular air cushion being formed about the top of the bottle. Removal of the seal allows a needle to be inserted through the stopper into the bottle.

While the protective container disclosed in EP-A-0 303 781 provides air cushions for protecting the bottle against breakage, other aspects of the container construction counteract its usefulness. For instance, the outer surface of the side of the container is smooth. Thus, the container can land on one of the longitudinal ribs causing the bottle to be compressed and break. In addition, one side of the seal contacts the bottle while the other side forms a tab which is proud of the top wall of the body part. Accordingly, an end-on impact will result in the bottle being compressed between the seal and the bottom wall of the base and breaking.

The hitherto proposed protective containers could also be improved in other areas to make them more user friendly. As an example, it is not always easy to hold the protective container and to insert a syringe needle through the container aperture into the stopper. It would therefore be useful to provide an alternative means for discharging a dose of the fluid medicament from the receptacle housed in the protective container.

In this connection, it is previously known to use a nozzle accessory for discharging the fluid medicament contained in a receptacle having a rubber stopper held in place by an annular metal crimp. The nozzle accessory has an outer sleeve which is mounted on a central, tubular spike so that a sharp distal tip of the spike protrudes distally from the sleeve. The sleeve has a distal end which is split into a plurality of resilient finger elements, each finger element having an inwardly directed flange. As the accessory is manoeuvred so that the sharp distal tip pierces the rubber stopper to provide a discharge path for the fluid medicament through the spike, the resilient fingers are forced over the crimp to cause the flanges to engage the underside of the crimp thereby connecting the accessory to the receptacle.

It would also be useful to provide a means for hanging the protective container to make it easier to access the stopper of the receptacle.

In this connection, it is also previously known to provide a protective container for housing a fluid medicament receptacle of the type referred to above having a fixed hanger for hanging the container which is located in a recess in a surface of the container so as not to protrude from the surface.

It is an aim of the present invention to improve the ability of protective containers to protect the article contained therein from breakage in the event of the protective container being dropped.

It is further an aim of the present invention to provide a protective container which is more user friendly.

SUMMARY OF THE INVENTION

According to a first aspect of the present invention there is provided a protective container for a fragile article having a forward end surface, a rear end surface, a side surface which extends endwise from the forward end surface to the rear end surface, a cavity between the surfaces for housing the fragile article and an endwise extending central axis, the side surface having maximum dimensions transverse to the central axis at forward and rear positions at, or adjacent to, the forward and rear end surfaces, respectively, so that the protective container lands on the forward and rear positions if dropped onto its side on an endless planar surface, and the forward and rear positions being adapted to absorb impact energy in the event of an impact thereon.

Preferably, the side surfaces at the forward and rear positions are adapted to deflect inwardly towards the central axis in response to a side-on impact.

The side surface of at least one of the forward and rear positions may be presented by a rim of a circumferentially-oriented protuberance. The or each protuberance can be formed by a trumpet-like profile of the side surface. Preferably, the or each protuberance has a re-entrant zone underneath the rim. Typically, the or each re-entrant zone will extend into the protuberance towards the end surface remote therefrom.

Preferably, the protuberance, or one of the protuberances, is a forward protuberance at the forward end surface, the forward end surface has an outer perimeter and the rim of the forward protuberance is contiguous with the outer perimeter. In this case, a recess may be formed in the forward end surface to form the re-entrant zone with the outer perimeter of the forward end surface forming a lip between the rim and the recess.

If access is needed to the fragile article, e.g. to dispense contents contained therein, an aperture may be formed in the forward end surface for access to the cavity. In this case, it is preferable that a closure is provided for closing the aperture, particularly a closure which is secured to the protective container and movable between a closed position in which it closes the aperture and an open position in which it opens the aperture.

The recess in the forward end surface may be a first recess which defines an annular channel about a boss in the forward end surface in which a second recess is formed. The aperture may be formed in the base of the second recess and the closure may lie in the second recess.

Preferably, the protuberance, or one of the protuberances, is a rear protuberance the rim of which is spaced forward of the rear end surface and a lip is formed between the rim of the rear protuberance and the re-entrant zone which is spaced forward of the rear end surface. The re-entrant zone may form an annular channel in the side surface.

Preferably, at least one of the re-entrant zones has a plurality of circumferentially spaced reinforcing ribs disposed therein.

Preferably, the protective container comprises a rear part which includes the rear end surface and a forward part which is securable to the rear part, the forward part being hollow and having an opening in a rear end thereof. The rear protuberance may be located at the outer perimeter of the opening.

At least one of the circumferentially-oriented protuberances may be an endless ring or a broken ring of discrete beads.

Ideally, the protective container further comprises a forwardmost retaining surface in the cavity against which the article rests when the protective container is inverted and a rearmost retaining surface in the cavity against which the article rests when the protective container is oriented forwardly with the forwardmost retaining surface being spaced rearward of the forward position and/or the rearmost retaining surface being spaced forward of the rear position. This configuration improves the impact resistance of the protective container To enable the fragile article and any identifying labels thereon to be observed, it is preferable for the protective container to be transparent. The protective container may be made from a plastics material, preferably polypropylene.

In a second aspect of the invention there is provided a package comprising a protective container according to the first aspect and a fragile article housed in the cavity.

According to a third aspect of the invention there is provided a package comprising a protective container having a wall structure which has an outer surface and an inner surface which bounds a cavity and a fragile receptacle housed in the cavity, at least a section of the outer surface having a corrugated configuration of ribs and depressions, the depressions being in registration with sections of the inner surface which are adapted to act on the receptacle to position the receptacle in the cavity and the ribs of the corrugated configuration being adapted to absorb impact energy in the event of an impact thereon to protect the fragile receptacle from breakage.

The corrugated configuration may be so dimensioned and constructed that the protective container will only land on the ribs in the event of the section of the wall structure falling onto an endless planar surface.

Preferably, the inner surface of the wall structure has a corrugated configuration of ribs and depressions, the ribs on the inner surface being adapted to act on the receptacle to position the receptacle in the cavity, the depressions on the inner surface being spaced from the receptacle and the ribs and depressions on the inner surface being, respectively, offset from the ribs and depressions on the outer surface.

For convenience, the section of the wall structure may have a corrugated configuration.

Preferably, the outer surface of the wall structure provides the protective container with a base, a top and a side and the at least a section of the wall structure is the side. The ribs and depressions of the corrugated configuration or configurations may then extend in a direction from the base to the top or transversely to that direction. The protective container may comprise a container part on which the corrugated configuration is formed, a base part insertable into the container part and securing means for locking the container and base parts together. The securing means may comprise co-operable securing elements on the container and base parts, the securing elements of the container part being disposed on the inner surface of the wall structure, preferably on the ribs on the inner surface of the wall structure.

According to a fourth aspect of the invention there is provided a package comprising a protective container having a forward end, a rear end and a cavity, and a receptacle which contains contents disposed in the cavity of the protective container such that a dispensing end of the receptacle for dispensing the contents is located facing the forward end, the forward end having an opening which allows the contents of the receptacle to be dispensed from the dispensing end of the receptacle out of the protective container, and a hanging member being secured to the protective container and movable from a stowed position to a deployed position in which the protective container is able to be hung from the hanging member in an inverted position.

Preferably, a recess is formed in the rear end and the hanging member is stowed in the recess when in the stowed position.

If the receptacle is fragile, it is preferable that the rear end of the protective container has a seating surface about the recess, the hanging member is positioned forward of the seating surface when in the stowed position and the seating surface is presented by an impact energy absorbing section of the rear end which is adapted to absorb impact energy in the event of an impact on the rear end to protect the fragile receptacle from breakage. As an example, the impact energy absorbing section may have an inner surface which forms a boundary surface of the cavity which is spaced rearwardly from the fragile receptacle when the protective container is seated on the seated surface. The space between the boundary surface of the cavity and the receptacle may be left void.

Preferably, the recess has an inner surface which forms a boundary surface of the cavity on which the receptacle sits when the protective container is seated on the seating surface. In this case, the boundary surface formed by the recess is preferably spaced forward of the boundary surface formed by the impact energy absorbing section.

Preferably, the recess is provided with a securing arrangement for releasably securing the hanging member in the stowed position.

According to a fifth aspect of the invention there is provided a package comprising a protective container having a forward end, a rear end, a side and a cavity between the ends and side and a fragile receptacle housed in the cavity having contents and a dispensing end for dispensing the contents facing the forward end of the protective container, the forward end of the protective container having an aperture therein for access to the dispensing end of the fragile receptacle, the protective container having a closure secured thereto which is movable between a closed position in which the closure closes the aperture and an open position in which the aperture is open, and the protective container being provided with a latch mechanism for latching the closure in the open position.

Preferably, the closure extends rearwardly when latched in the open position. The latch mechanism may comprise co-operable male and female parts, for instance an aperture and a protuberance for engaging the aperture to latch the closure in the open position.

According to a sixth aspect of the invention there is provided a protective container having an element which is movable between a stowed position, in which the element lies against a surface of the container, and a deployed position, in which the element extends away from the surface, and a label which has one or more first sections affixed to the surface of the container and which, prior to first movement of the element from the stowed position to th deployed position, has a second section detachably connected to the or each first section and affixed to the element, whereby on first movement of the element from the stowed position to the deployed position the second section is detached from the or each first section and whereby on movement of the element back to the stowed position the label is re-formed. The or each detachable connection may be in the form of a tear line.

The protective container may have a cavity for storing a substance to be dispensed from the container and an aperture in the surface from which the substance is able to be dispensed. The element may then be a closure connected to the container which, in the stowed position, closes the aperture, and which, in the deployed position, opens the aperture.

According to a seventh aspect of the invention there is provided a protective container having a cavity for housing an article, the cavity having a boundary surface from which depends a skirt formed by two or more discrete skirt portions each having inner and outer surfaces, the skirt portions being adapted so that the inner surfaces thereof enclose a structural feature of the article when housed in the cavity, and the outer surface of each skirt portion being provided with one or more buttresses to provide the skirt portions with resistance to outward deflection thereof. The protective container may form part of a package in which a receptacle is housed in the container with a dispensing end of the receptacle being enclosed by the skirt portions. The boundary surface of the cavity would then have an aperture therethrough to provide access to the dispensing end of the receptacle.

In an eighth aspect of the invention there is provided use of a protective container according to the first, sixth and seventh aspects as a container for a fragile article.

According to a ninth aspect of the present invention there is provided an accessory for a container structure having a chamber for a fluid substance and a piercable closure to the chamber, the accessory having a connector section adapted to connect the accessory to the container structure in an operational position, a piercing section for piercing the piercable closure when the accessory is in the operational position, a passageway for passage of the fluid substance from the chamber into the accessory when in the operational position, and an axis of rotation about which the connector section is rotatable from a first angular disposition in which the connector section is not connectable to the container structure to a second angular disposition in which the connector section is able to connect the accessory to the container structure in the operational position.

In an embodiment such as hereinafter to be described, the container structure comprises inner and outer containers, the inner container being contained in the outer container and having the chamber and the piercable closure, and the outer container having an aperture aligned with the piercable closure on the inner container through which the piercing section is able to project in the operational position of the accessory.

Typically, the piercing section has an inlet opening of the passageway. Preferably, the connector section is rotatable about the axis of rotation relative to the piercing section. More preferably, the connector section is rotatable between the first and second angular dispositions at a fixed axial position. Even more preferably, the connector section is adapted to releasably connect the accessory to the container structure in the operational position.

The connector section may have a locking feature at an outer circumferential perimeter of the connector section for engaging with a complementary locking feature of the container structure. Preferably, the locking feature is outwardly directed, for instance in the form of one or more extensions at the outer circumferential perimeter of the connector section. The locking feature may be at least a part of an endless flange at the outer circumferential perimeter. Alternatively, the locking feature may take the form of one or more recesses formed in the outer circumferential perimeter of the connector section.

Preferably, the locking feature is located on a part of the outer circumferential perimeter which overlies (or shadows) different areas when in the first and second angular dispositions. More preferably, in the first angular disposition the outer circumferential perimeter overlies a first area, in the second angular disposition the outer circumferential perimeter overlies a second area which has discrete segments arranged about the axis of rotation which extend beyond the first area and the locking feature is located on a part of the outer circumferential perimeter which forms the discrete segments.

The locking feature may comprise one or more pairs of locking elements which are arranged on opposed sides of the axis of rotation.

Preferably, the outer circumferential perimeter describes a curvilinear path when rotated about the axis of rotation, for example a circular path. The outer circumferential perimeter may have a non-round profile. The outer circumferential perimeter may further have a plane of symmetry through the axis of rotation, and the axis of rotation may be a centre of symmetry for the outer circumferential perimeter.

Preferably, the connector section is fixed, or substantially fixed, against axial movement relative to the piercing section.

Ideally, the accessory comprises a piercing part and a connector part rotatably mounted to the piercing part, the connector part having the connector section and the piercing part having the piercing section.

The accessory may be a nozzle accessory with the passageway adapted to discharge the fluid substance in the chamber of the container structure through the nozzle accessory when in the operational position. In this case, the accessory may further have an outlet section which has an outlet opening of the passageway and which may be adapted to receive a tube in fluid communication with the outlet opening of the passageway. To this end, the outlet section may be adapted to form an interference fit with the tube, for instance by having a roughened outer surface, which may be a circumferentially oriented roughness such as in the form of at least one barb.

Ideally, the connector section is rotatable relative to the outlet section. To this end, the piercing part may have the inlet and outlet sections and the passageway. The piercing part may extend through the connector part.

Preferably, the accessory is adapted such that the piercing section pierces the piercable closure when the connector section is located in a predetermined axial position and at the first angular disposition and such that the connector section is able to rotate to the second angular disposition when at the predetermined axial position.

In a tenth aspect of the invention there is provided a container system comprising a container structure having a chamber for holding a fluid substance and a piercable closure to the chamber and an accessory according to the ninth aspect of the invention, the container structure having a connector section which is co-operable with the connector section of the accessory to fix the accessory to the container structure in the operational position with the piercing section piercing the piercable closure of the container structure only when the connector section of the accessory is in the second angular disposition.

In an eleventh aspect of the invention there is provided a container system comprising a container structure having a chamber for holding a fluid substance, a piercable closure to the chamber and a connector section; and an accessory having a connector section adapted to co-operate with the connector section of the container structure to connect the accessory to the container structure in an operational position, a piercing section for piercing the piercable closure when the accessory is in the operational position and a passageway for passage of the fluid substance from the chamber into the accessory when in the operational position; the connector sections adapted to be:

(a) indexed together in an indexing position; and (b) moved relative to one another from the indexing position to a co-operating position in which the connector sections co-operate to connect the accessory to the container structure in the operational position.

In a twelfth aspect of the invention there is provided a container system comprising an inner container having a chamber which contains a fluid substance and a piercable closure to the chamber; an outer container structure having a chamber for housing the inner container, a connector section and an aperture in the connector section which faces the piercable closure when the inner container is housed in the outer container structure; and an accessory having a connector section adapted to co-operate with the connector section of the outer container structure to connect the accessory to the outer container structure in an operational position, a piercing section so dimensioned and arranged that when the accessory is in the operational position the piercing section projects through the aperture to pierce the piercable closure on the inner container when housed in the outer container structure, and a passageway for passage of the fluid substance into the accessory when in the operational position with the piercing section piercing the piercable closure.

Preferably, the connector sections are adapted to co-operate for releasable connection of the accessory in the operational position. The connector sections may be interengagable sections of the container structure and the accessory.

The connector sections of the container systems of the tenth and twelfth aspects of the invention are preferably adapted to be indexed together in an indexing position and to be moved relative to one another from the indexing position to bring the accessory to the operational position.

The connector sections of the container systems of the invention may be adapted to be rotated relative to one another from the indexing position to bring the accessory to the operational position.

Preferably, one of the connector sections has a recess and the other a seat for sitting in the recess to index the connector sections in the indexing position. One of the recess and the seat may have a male feature and the other a female feature, the male and female features interengaging with one another when the connector sections are moved relative to one another from the indexing position to connect the accessory to the container structure in the operational position. Preferably, the female feature is provided in the recess and, more preferably, comprises at least one slot with the male feature comprising an extension for, and sized to fit in, each slot.

The container systems of the tenth and eleventh aspects of the invention may have an outer container which has the connector section and an aperture in the connector section, and an inner container which contains the fluid substance and has the piercable closure, the aperture on the outer container being arranged such that in the operational position of the accessory the piercing section projects therethrough to pierce the piercable closure on the inner container.

The outer container of the container systems according to the invention may be a protective container according to the invention. The inner and outer containers of the container systems according to the invention may collectively be a package according to the invention.

According to a thirteenth aspect of the invention there is provided a container for use with an accessory according to the ninth aspect of the invention having a chamber for holding an inner container which contains a fluid substance and has a piercable closure thereto, an opening to the chamber, and a connector section adapted to connect with the connector section of the accessory to put the accessory in the operational position with the piercing section projecting through the opening to pierce the piercable closure. The container may take the form of a protective container according to the invention.

According to fourteenth aspect of the invention there is provided a container having a surface, a recess in the surface and a fixed hanger for hanging the container located in the recess so as not to protrude from the surface, the surface, recess and fixed hanger forming part of a releasable member of the container.

The fixed hanger may be a plate-like element having an aperture therethrough. Preferably, the plate-like element extends from one side of the recess to another side thereof. The surface may be bounded by sides and the recess take the form of an open-ended groove extending from one side of the surface to another side thereof. The container may have a chamber for containing an article and the recess an underside in the chamber on which the article seats when the container is oriented with the surface lowermost. The surface may be hollow to the sides of the recess. The surface may be a lower end surface of the container on which the container is adapted to sit, in which case the container may have a front end surface with an aperture therein for discharge of contents of the container.

A fifteenth aspect of the invention provides a protective container for an article having an outer wall structure which has an inner surface, an outer surface and a thickness between the inner and outer surfaces, and a cavity for housing the article bounded by the inner surface of the outer wall structure, at least a section of the outer wall structure having a corrugated configuration comprising an alternating series of ribs and depressions, the inner surface at the depressions being adapted in use to bear against the article when housed in the cavity, and the outer wall structure having a first thickness at the ribs and a second thickness at the depressions which is different from the first thickness.

Preferably, the first thickness is greater than the second thickness. The outer wall structure thickness at the ribs and depressions, respectively, is preferably generally uniform. If not, the first thickness may be a minimum thickness for the ribs and the second thickness a maximum thickness for the depressions.

Preferably, the at least a section of the outer wall structure is made from a flexible material.

Preferably, the corrugated configuration further comprises sidewalls which connect the ribs to the depressions and the outer wall structure has a third thickness at the sidewalls which is no greater than the first thickness, more preferably less than the first thickness, and preferably greater than the second thickness.

Preferably, the protective container according to the fifteenth aspect has a top, a base and a side and the outer wall structure has the corrugated configuration on the side. The ribs and depressions may extend in a direction between the top and the base.

In accordance with the present invention, each aspect thereof can be combined with one or more of the other aspects or features of one or more of the other aspects.

The protective containers, packages and container systems of the invention are ideal for use with a bottle, vial or ampoule containing a medicament, e.g. an antibiotic such as Micotil®.

By way of example, embodiments of the present invention will now be described with reference to the accompanying Figures of drawings.

BRIEF DESCRIPTION OF THE FIGURES OF DRAWINGS

FIG. 4 is a perspective view of a base part of the protective container;

FIG. 5 is a plan view of the base part;

FIG. 6 is a sectional view of the base part along line A—A in FIG. 5;

FIG. 7 is a sectional view of the base part along line B—B in FIG. 5;

FIG. 8 is a plan view of a container part of the protective container;

FIG. 9 is a sectional view of the container part along line C—C in FIG. 8;

Figures 16, 17:
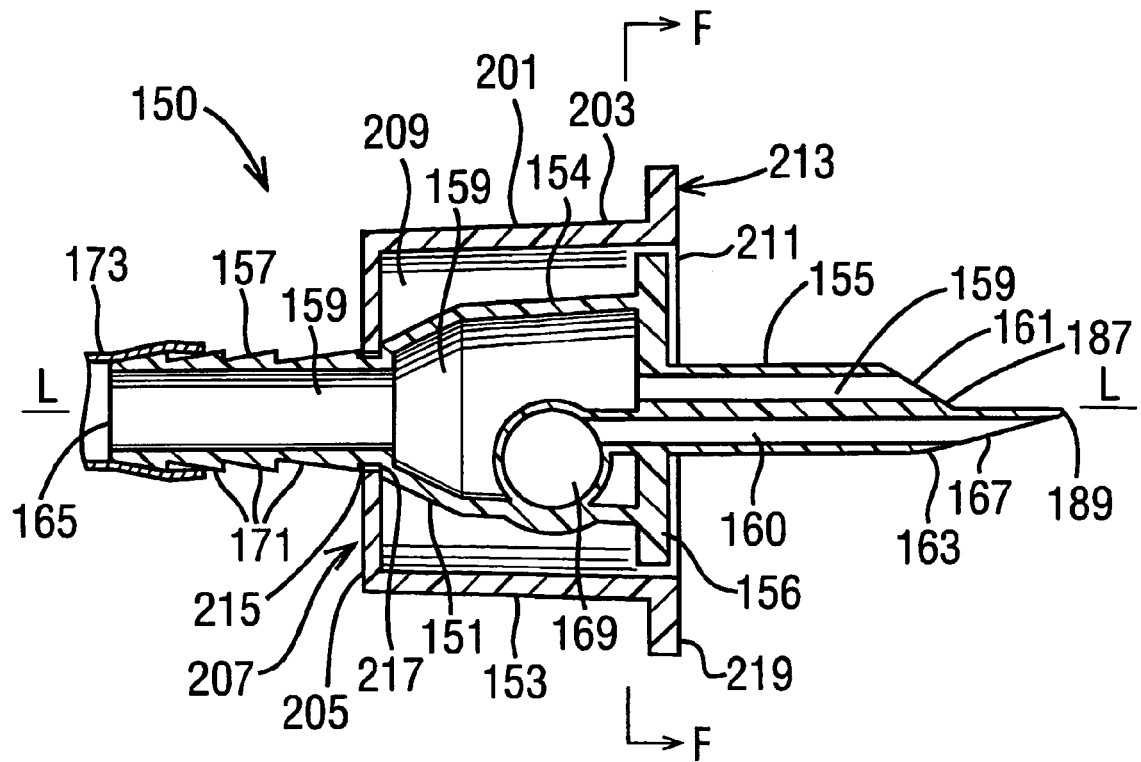
Figure 19A:
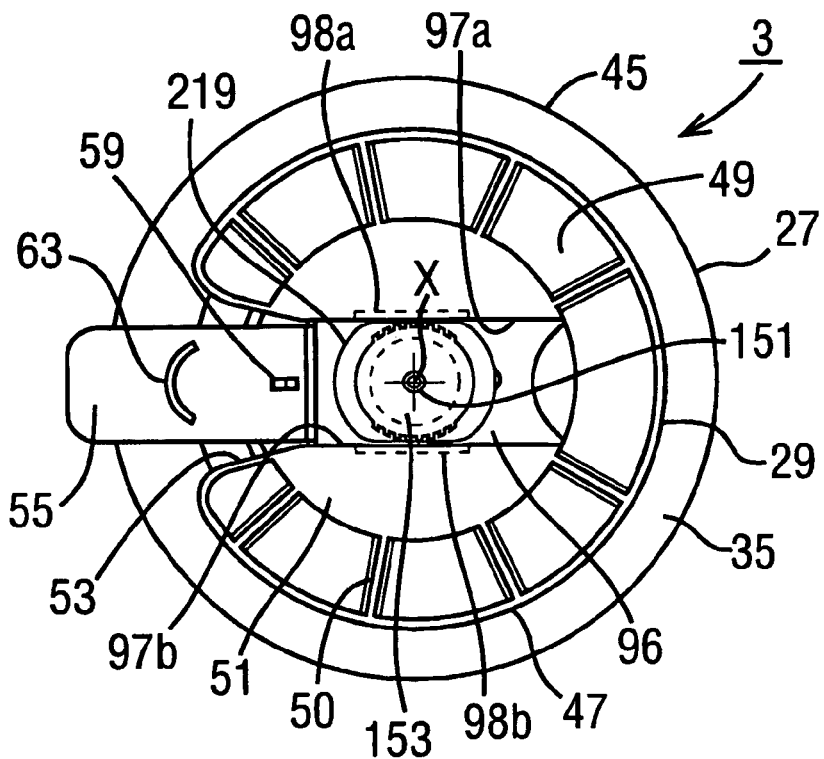
Figure 19B:
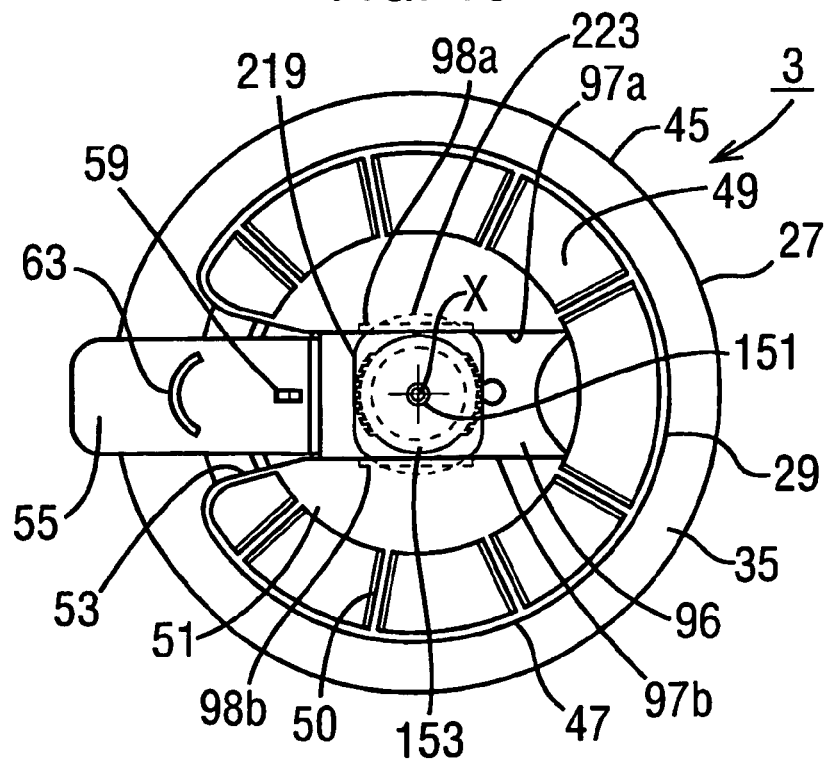
Figure 20:
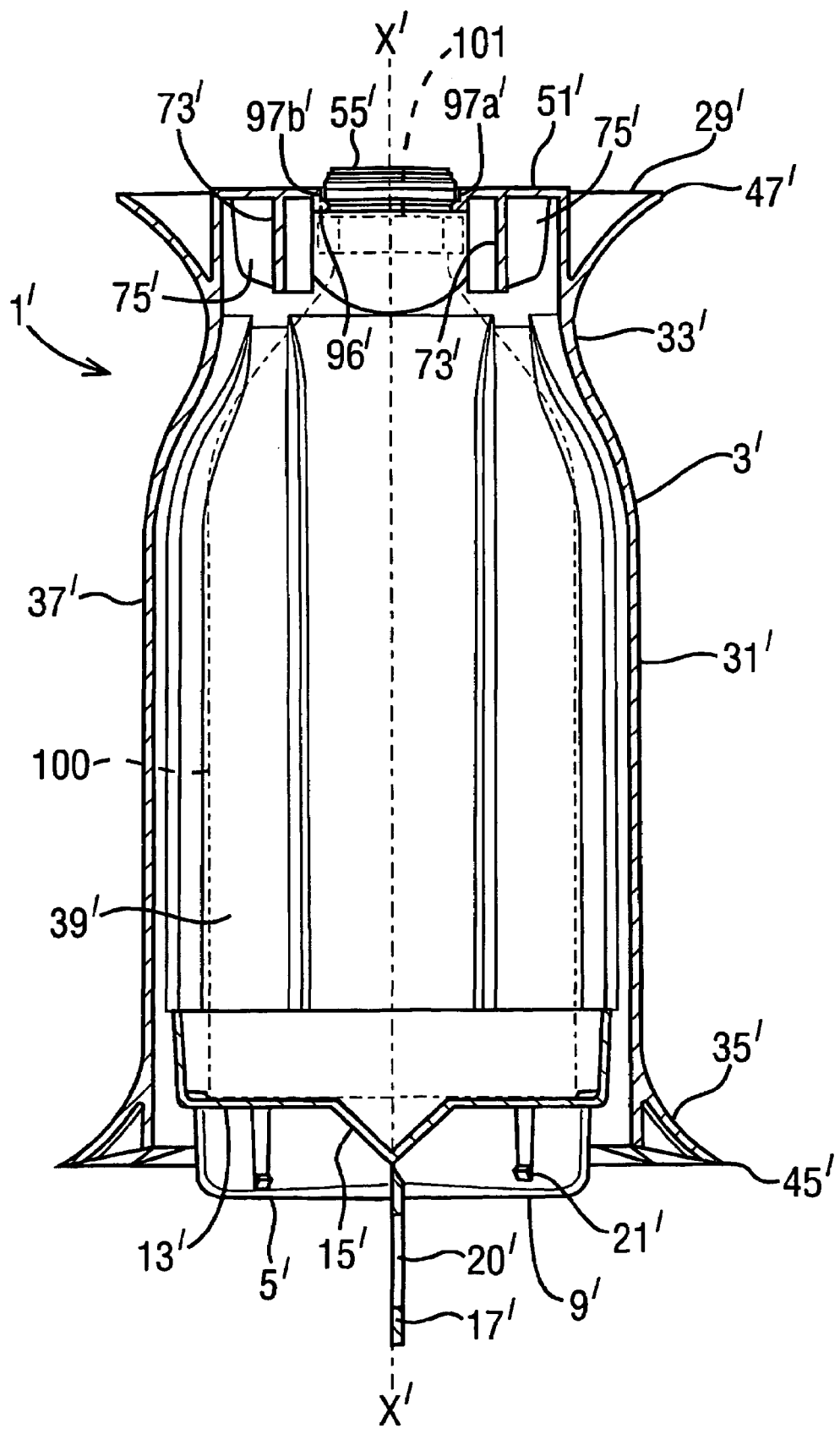
Figure 21:
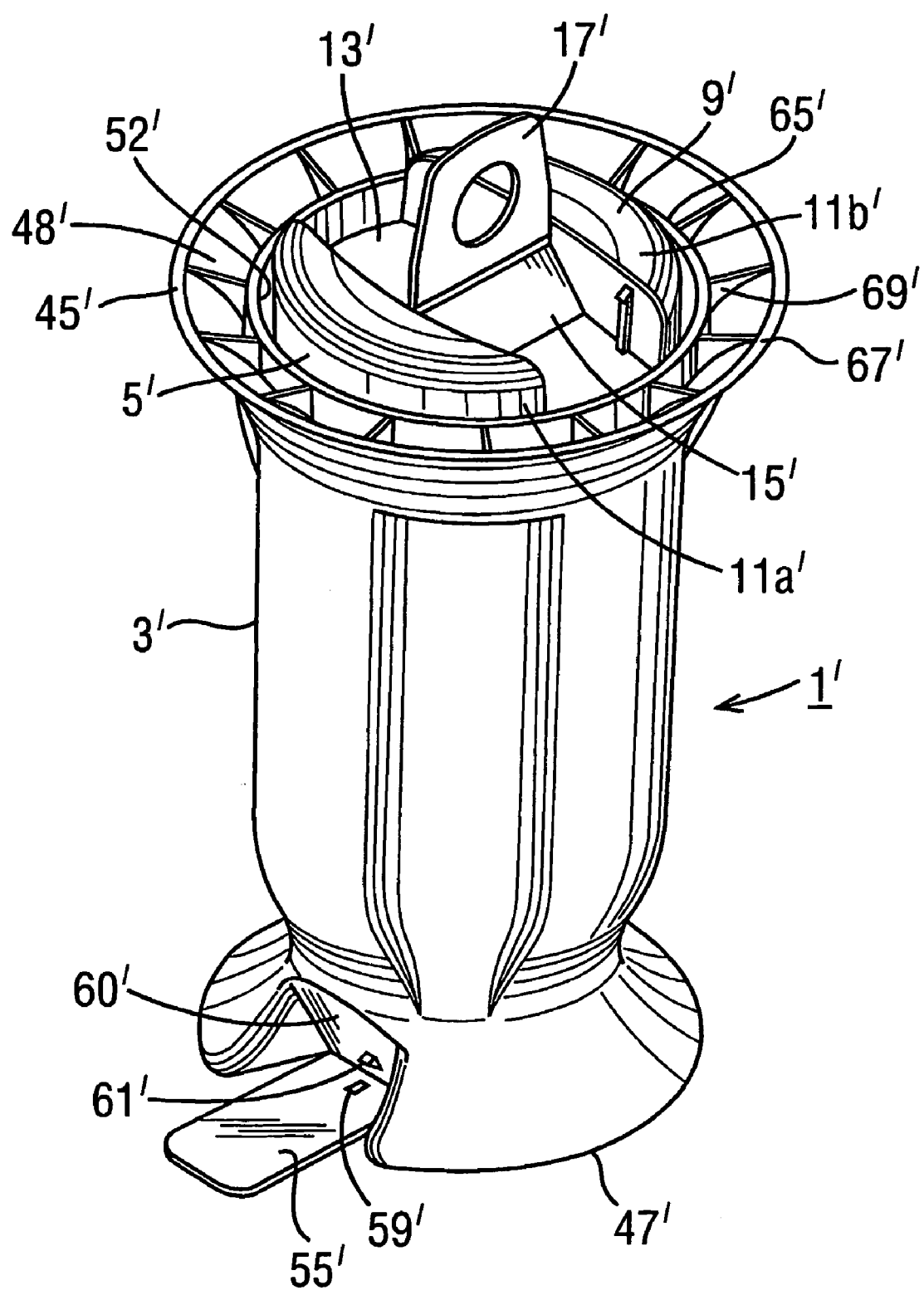
Figure 22:
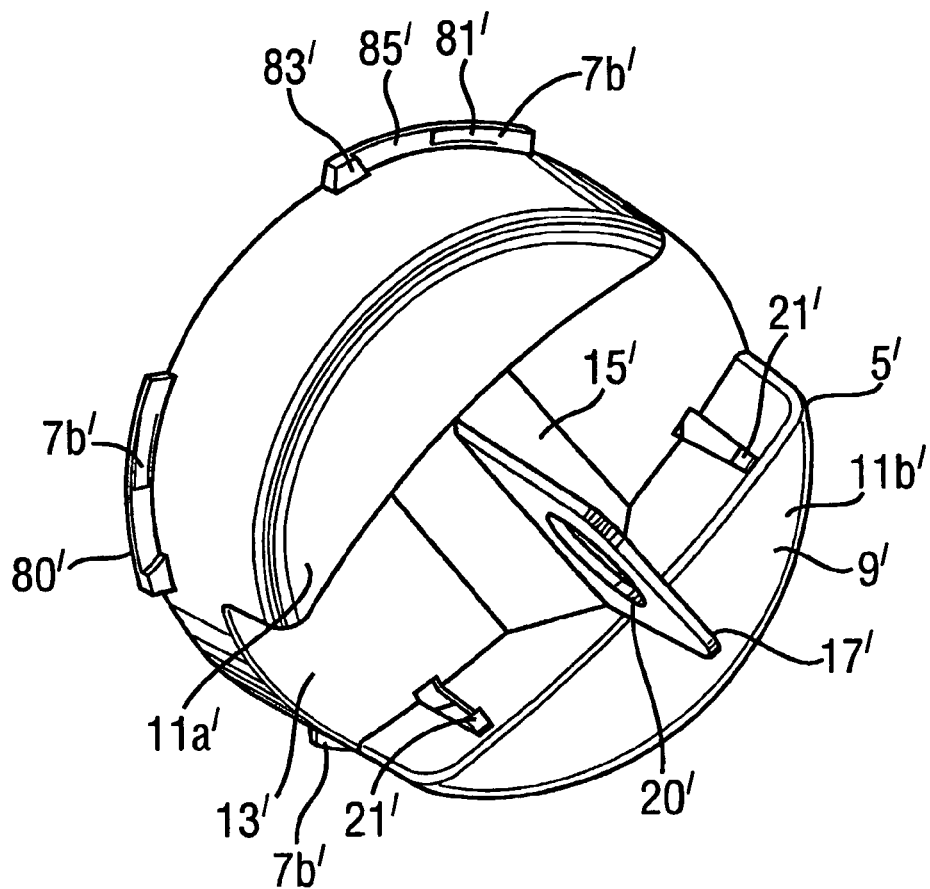
Figure 23:
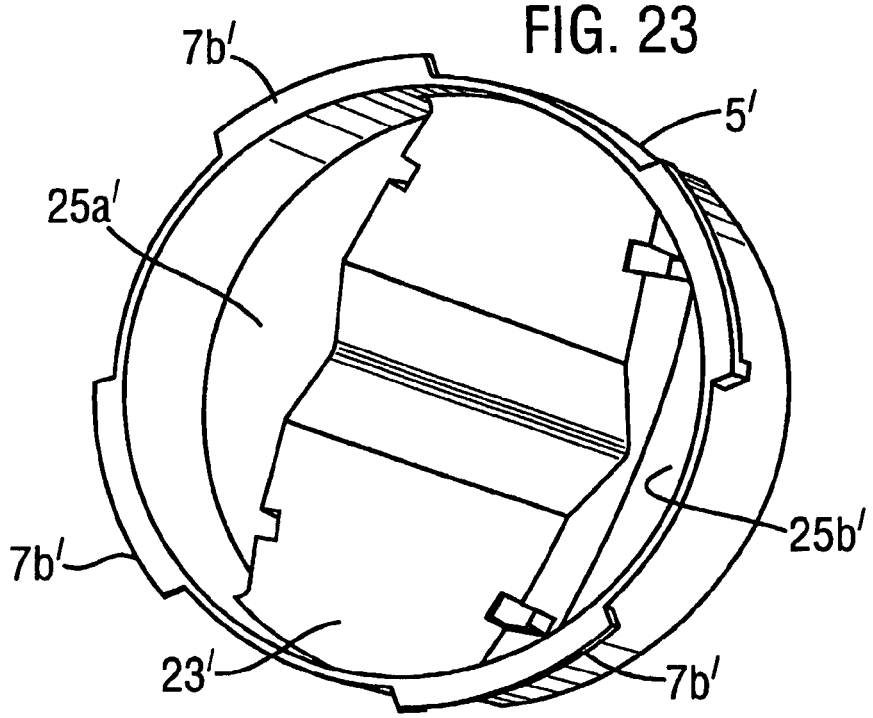
Figure 24:
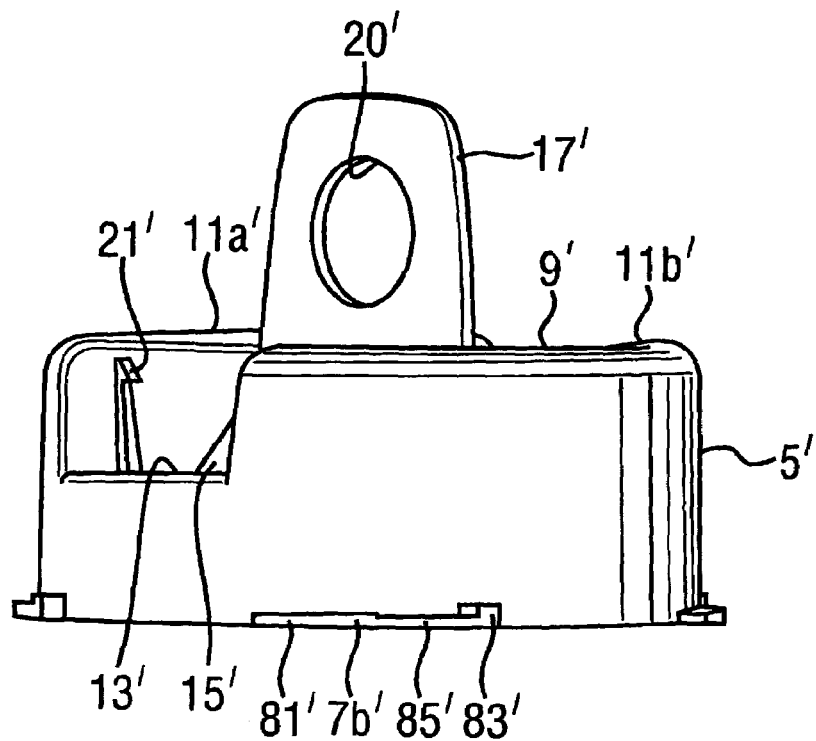
Figure 25:
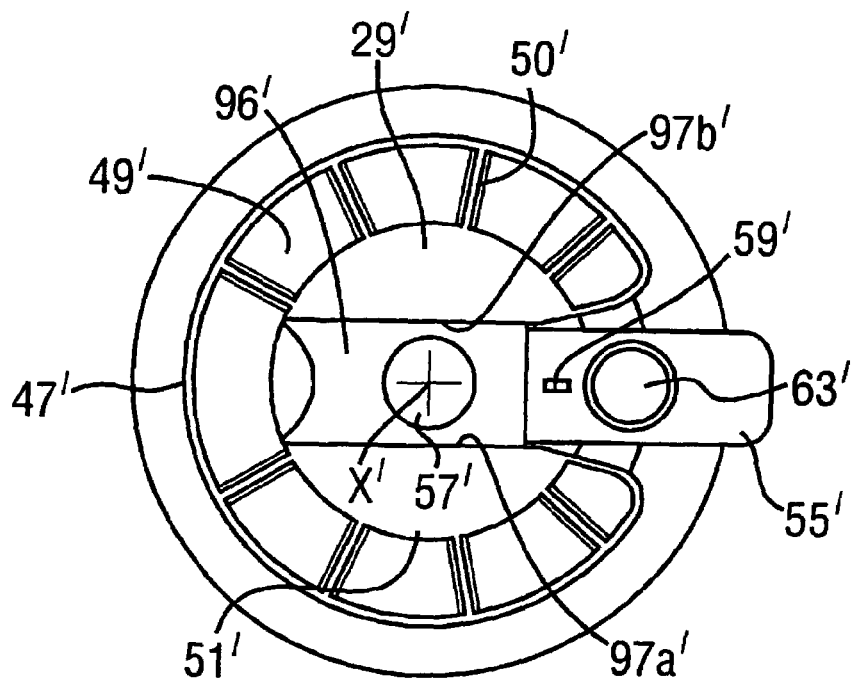
Figure 26A:
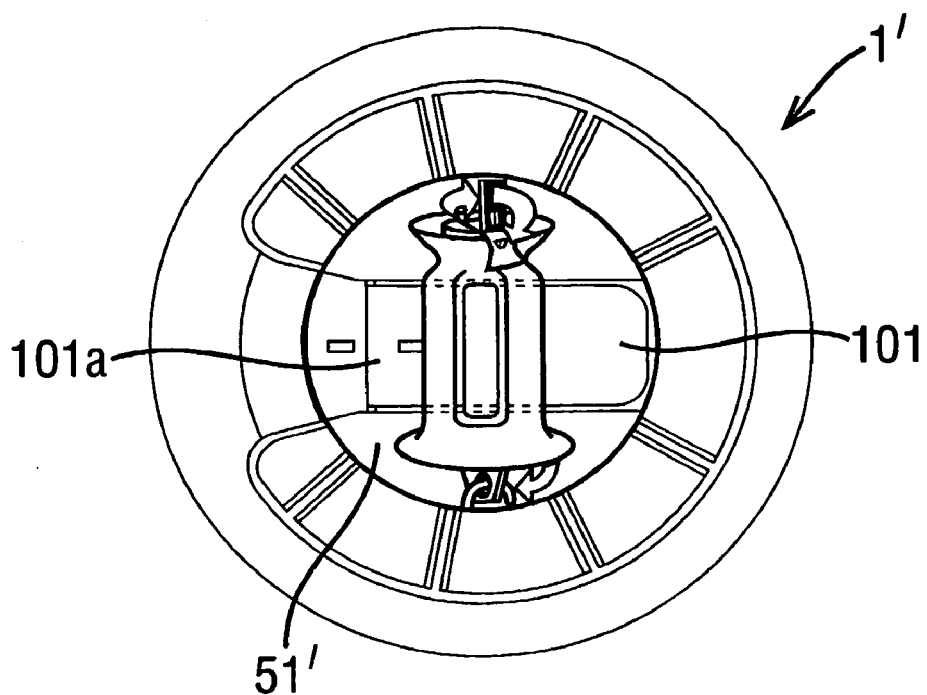
Figure 26B:
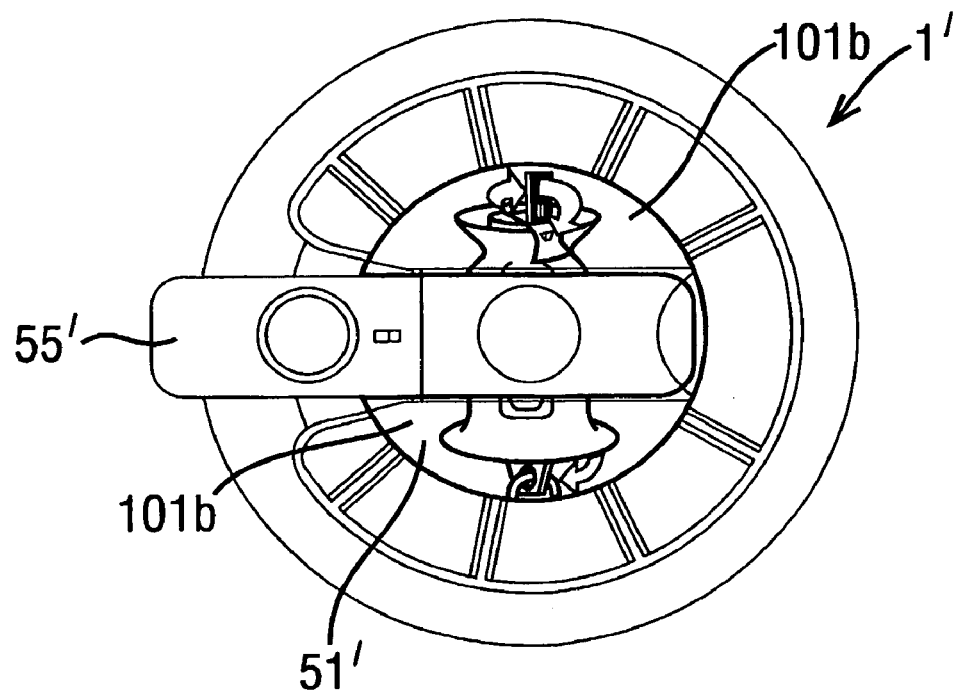

FIGS. 14A–C are schematic development views showing, in sequence, the interaction of locking elements on the base and container parts for locking the base and container parts together;

FIG. 15 is an exploded view of the nozzle accessory;

FIG. 16 is a sectional view of the nozzle accessory in its assembled state;

FIG. 17 is a sectional view along line F—F in FIG. 16;

FIG. 18 is an underneath plan view of a connector part of the nozzle accessory;

FIGS. 19A and 19B correspond to FIG. 8, but show the sequence of steps for connecting the nozzle accessory to the protective container;

FIG. 20 is a cross-sectional side view of an alternative protective container in accordance with the present invention;

FIG. 21 is a perspective view of the alternative protective container;

FIG. 22 is a view of an outer surface of a base part of the alternative protective container;

FIG. 23 is a view of an inner surface of the base part of FIG. 22;

FIG. 24 is a side view of the base part of FIG. 22;

FIG. 25 is a view of an upper end of a container part of the alternative protective container; and FIGS. 26A and 26B are views of a re-formable label on the upper end of the container part of the alternative protective container.

DETAILED DESCRIPTION OF THE EXEMPLARY EMBODIMENTS OF THE INVENTION

In the following description of different embodiments of the invention, like parts or features are assigned like reference numerals.

There now follows with reference to FIGS. 1 to 19 of the drawings a detailed description of a container system 200 in accordance with the present invention comprising a transparent, plastics protective container 1, a glass bottle 100 of liquid medicament to be housed in the protective container 1 and a nozzle accessory 150 for attachment to the protective container 1 to enable discharge of the liquid medicament from the bottle 100 by piercing a rubber stopper 101 of the bottle 100. As an example, the bottle 100 may contain 250 ml of the bovine respiratory disease antibiotic Micotil® (tilmicosin) of Eli Lilly. The combined weight of the medicament and the bottle 100 would typically be 450 g.

Figure 1:
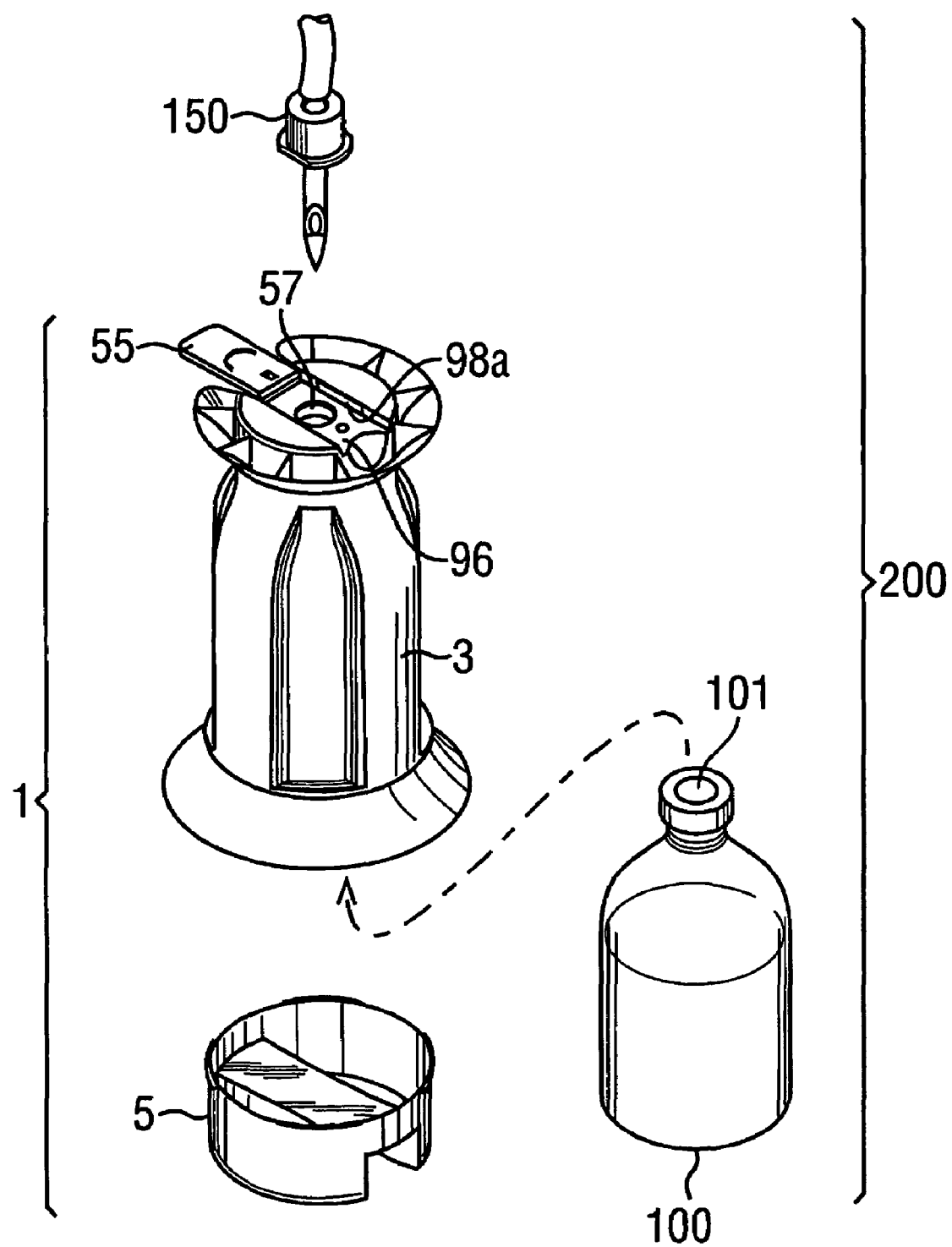
FIG. 1 is an exploded perspective view of a container system in accordance with the present invention comprising a protective container, a bottle and a nozzle accessory.
Figure 2:
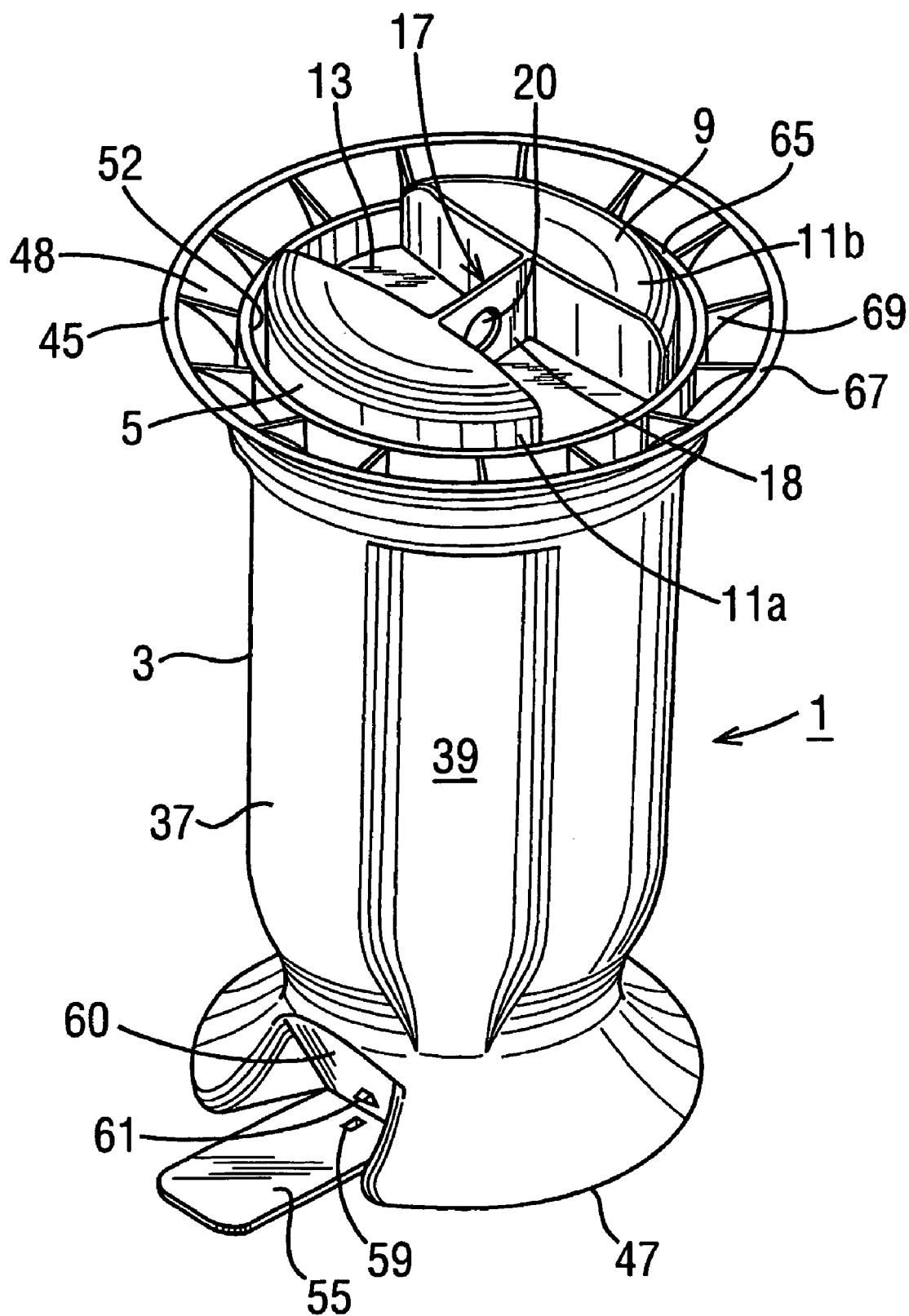
FIG. 2 is a perspective view of the protective container when assembled.
Figure 3:
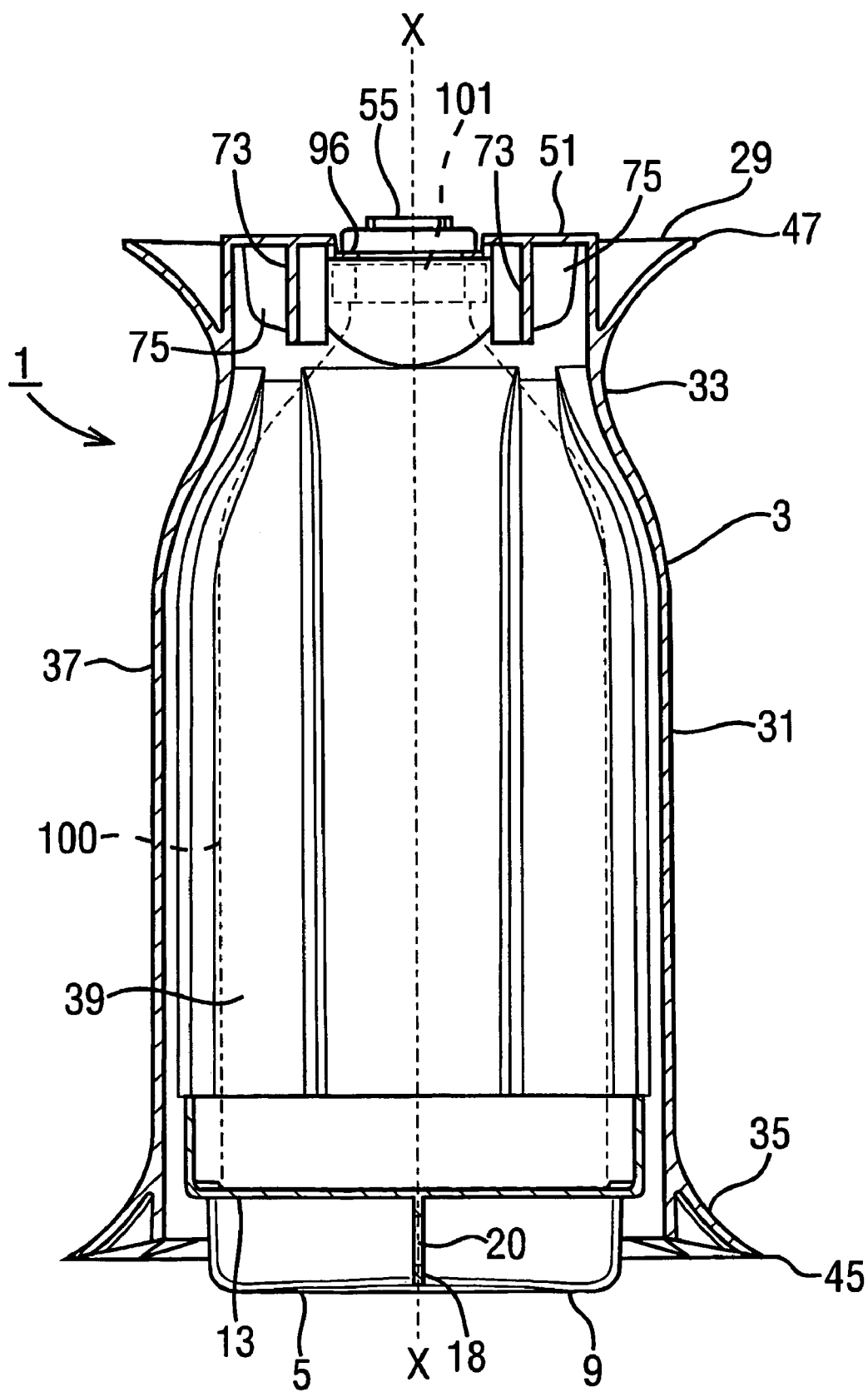
FIG. 3 is a cross-sectional side view of the protective container when assembled.

Turning first to FIGS. 1 to 3, it can be seen that the protective container 1 is of a generally cylindrical form with a central axis X and has two component parts, namely a container part 3 and a base part 5. Each part 3, 5 is defined by an outer wall structure having a different thickness for different features. Generally, the outer wall structure has a thickness in the range of approximately 1.0–2.0 mm, preferably in the range of 1.2–2.0 mm.

As shown in FIGS. 4, 5 and 9 to 12, the container and base parts 3, 5 carry interengagable locking elements 7a, 7b for releasably securing the container and base parts 3, 5 together. The protective container 1 is therefore re-usable and, moreover, allows the user to take out the bottle 100 for inspection.

Preferably, the protective container 1 is made from polypropylene by injection moulding and has a length of approximately 157 mm. Polypropylene is preferred as it deflectable to absorb impact forces. As an example, polypropylene is a more resilient material than polycarbonate, as used in the prior art.

Referring to FIGS. 4 to 7, the base part 5 has an outer seating surface 9 having a raised perimeter 10 on which the protective container 1 sits. The outer surface 9 is defined by a pair of diametrically opposed protrusions 11a, 11b spaced apart by a central channel 13. A fixed or static hanger 17 for hanging the protective container 1 in an inverted position is positioned in-between the protrusions 11a, 11b in the channel 13. The hanger 17 has a narrow strut 18 which is connected at its opposed ends to the protrusions 11a, 11b and an aperture 20 in the strut 18 for hanging the protective container 1 on a hook or the like. The strut 18 has a cross-sectional profile which tapers inwardly in a direction extending from the channel to the outer surface 9. Thus, the strut 18 has a greater thickness at its base than at its free end. As will be seen from FIGS. 6 and 7, the hanger 17 does not protrude from the channel 13 and hence is disposed below the level of the raised perimeter 10. In this way, the hanger 17 does not interfere with the base part 5 being used as a seat for the protective container 1.

Turning to FIG. 7, it can be seen that the protrusions 11a, 11b are hollow. In this way, a bottom 103 of the bottle 100 sits on the inner surface 23 of the channel 13, not the inner surfaces 25a, 25b of the protrusions 11a, 11b. The reason for this is simple. If the protective container 1 is dropped on its base part 5 it will land on the raised perimeter 10 of at least one of the protrusions 11a, 11b. As the protrusions 11a, 11b are hollow and separated by the channel 13, they will deflect towards the container part 3 and radially outwardly/inwardly to absorb the impact forces. As the hanger 17 is disposed below the level of the raised perimeter 10, the hanger 17 does not impact the ground. Accordingly, the hanger 17 does not transmit impact forces to the inner surface 23 of the channel 13 on which the bottle 100 is supported. Thus, the likelihood of breakage of the bottle 100 is reduced. In fact, testing under National Safe Transit Association (NSTA) guidelines for packages weighing under 45.36 kg (100 lb) has shown that the protective container 1 is able to keep the bottle 100 free from damage and retain its integrity so as to provide further protection for the bottle 100 when dropped by a drop tester onto a concrete surface on its base part 5 from a height of 0.762 m (30 in).

On the outer circumference of the base part 5 there are formed the locking elements 7b which co-operate with the locking elements 7a in the container part 3 for releasably locking the container and base parts 3, 5 together.

Referring now to FIGS. 2, 3 and 8 to 13, the container part 3 has a lower open end 27 in which the base part 5 is releasably securable, an upper end 29 and a cylindrical body 31 in-between. As shown particularly well in FIGS. 3, 9 and 10, a flared or waisted neck 33 connects the body 31 to the upper end 29 and a flared collar 35 connects the body 31 to the lower open end 27. This gives the outer surface of the container part 3 an ergonomic trumpet-like profile which makes it easier for the user to grip the protective container 1 and reduces the risk of self-injection.

The body 31 is corrugated, being provided with a series of longitudinal panels in the form of alternating ribs 37 and depressions 39. As will be understood by reference to FIGS. 11 and 12, the inner surfaces 41 of the depressions 39 bear against the side surface of the bottle 100 but the inner surfaces 43 of the ribs 37 are spaced radially outwardly from the side surface of the bottle 100 to create longitudinal spaces between the ribs 37 and the bottle 100. The panels 37, 39 serve two functions, namely providing a gripping surface for the holder and impact resistance for the bottle 100 in the event of the side of the protective container 1 falling onto an edge or short planar surface.

In relation to the latter function, the impact resistance is provided by the ribs 37 as these will absorb side-on impact energy by deflecting into the space created between them and the bottle 100. Improved impact resistance is provided by making the outer wall structure of the container part 3 have a first thickness t1 for the ribs 37 and a second thickness t2, which is less than the first thickness t1, for the depressions 39. The side wall connecting the ribs 37 and depressions 39 preferably has a third thickness t3 intermediate the first and second thicknesses t1, t2. This is shown schematically in FIG. 11. As an example, the first thickness t1 may be approximately 1.4 mm, the second thickness may be approximately 1.2 mm and the third thickness may be approximately 1.3 mm.

In this embodiment of the invention the panels 37, 39 are relatively wide so as to (i) enable a label (not shown) on the bottle 100 to be easily observed without interference from the edges of the panels 37, 39, and (ii) provide greater flexibility. Consequently, this raises the possibility of the protective container 1 landing on one of the depressions 39 instead of the ribs 37. As the depressions 39 are in direct contact with the bottle 100, the bottle 100 might break in this instance.

For this reason, the body 31 of the container part 3 is connected to the upper 29 and lower ends 27 with the flared connecting portions 33, 35 to result in the opposed ends 27, 29 having collars or ribs 45, 47 whose rims sit proud of the outer surface of the body 31. The diameters of the collars 45, 47 are approximately 104 mm and 86 mm respectively. These compare with a diameter of about 80 mm for the body 31. Having a smaller diameter for the collar 47 at the upper end 29 than the diameter of the collar 45 at the lower open end 27 improves the mouldability of the container part 3.

If the protective container 1 falls side-on onto a long planar surface it will land on the collars 45, 47 as opposed to one of the depression panels 39. The collars 45, 47 are adapted to deflect radially inwardly so as to absorb side-on impact forces and provide protection for the bottle 100 against breakage. Testing under NSTA guidelines for packages weighing under 45.36 kg (100 lb) has shown that the protective container 1 is able to keep the bottle 100 free from damage and retain its integrity so as to provide further protection for the bottle 100 when dropped by a drop tester onto a concrete surface on its side from a height of 0.762 m (30 in).

The ability of the collar 47 at the upper end 29 of the container part 3 to deflect to absorb side-on impact forces can be explained with reference to FIGS. 8 and 10. The upper end 29 of the container part 3 is provided with an annular channel 49 adjacent the outer perimeter of the upper end 29. This results in a re-entrant zone or undercut being formed underneath the rim of the collar 47 into which the collar 47 can deflect. This construction also enables the collar 47 to deflect towards the lower end 27 to absorb impact forces resulting from dropping the protective container 1 on its upper end 29 and thereby provide end-on impact protection for the bottle 100. To prevent the collar 47 from deflecting inwardly too much, the annular channel 49 is provided with a plurality of radial, reinforcing ribs 50.

Figure 10:
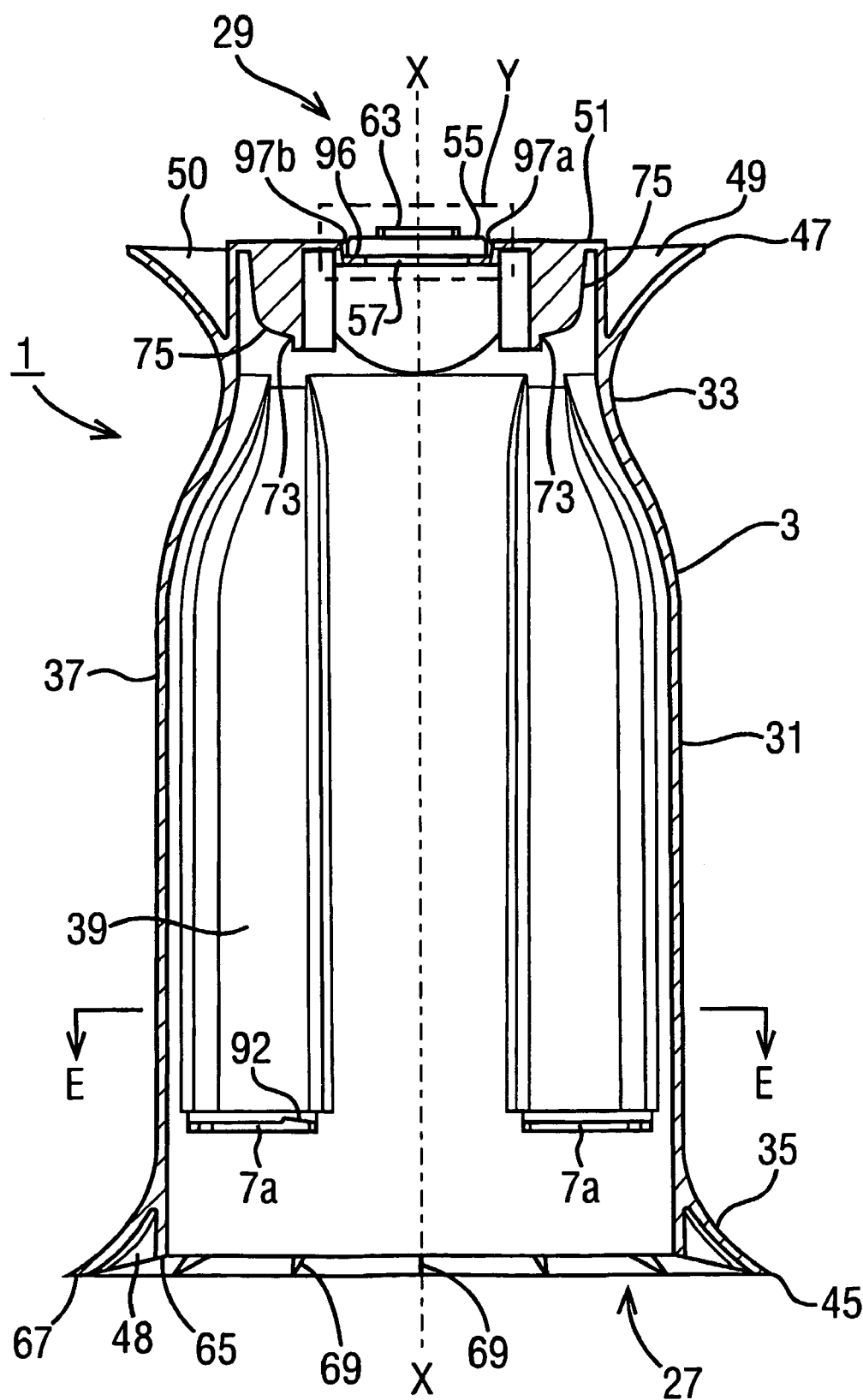
FIG. 10 is a sectional view of the container part along line D—D in FIG. 8.

Similarly, it can be seen from FIGS. 2 and 10 that the open lower end 27 of the container part 3 has inner 65 and outer 67 circumferential walls which define an annular channel 48 therebetween. The outer circumferential wall 67 presents the rim of the collar 45 and the annular channel 48 gives a re-entrant zone for the collar 45 to deflect into. The inner and outer circumferential walls 65, 67 are connected by radial reinforcing ribs 69 to control the degree of deflection of the rim of the collar 45. From FIG. 2 it will also be seen that an annular space 52 is also formed between the inner circumferential wall 65 and the outer side surface of the base part 5 when the container and base parts 3, 5 are secured together. This annular space 52 provides room for the inner circumferential wall 65 to deflect into if need be.

Returning to FIGS. 3 and 8 to 10, the annular channel 49 in the upper end 29 of the container part 3 extends about a cylindrical boss 51 in the centre of the upper end 29. A slot 53 is formed in the collar 47 to enable a flap 55 which is hingedly connected to the boss 51 to be hinged open to expose an aperture 57 in the boss 51. The aperture 57 allows access to the rubber stopper 101 in the dispensing end of the bottle 100. The flap 55 has an aperture 59 therein which, as will be understood from FIGS. 2 and 9, is able to latch to a protrusion 61 on a bevel surface 60 of the container part 3 and releasably secure the flap 55 in an open position in which it extends through the slot 53 in a direction towards the lower end 27 of the container part 3. In this manner, the flap 55 is re-closable, especially important if the bottle 100 contains a multiple dose of the medicament, and kept out of the user's way when mounting the nozzle accessory 150 to the upper end 29 of the protective container 1, as will be described in more detail hereinafter. The flap 55 is secured in the closed position through an interference fit between an arcuate rib 63 on its underside and the boss aperture 57.

As shown in FIGS. 3 and 10, the outer surface of the boss 51 is slightly proud of the collar 47. Thus, if the protective container 1 lands end-on it will impact the boss 51. The rubber stopper 101 in the bottle 100, though, acts to absorb the impact forces transmitted to it by the boss 51 to protect against bottle breakage.

Figure 12:
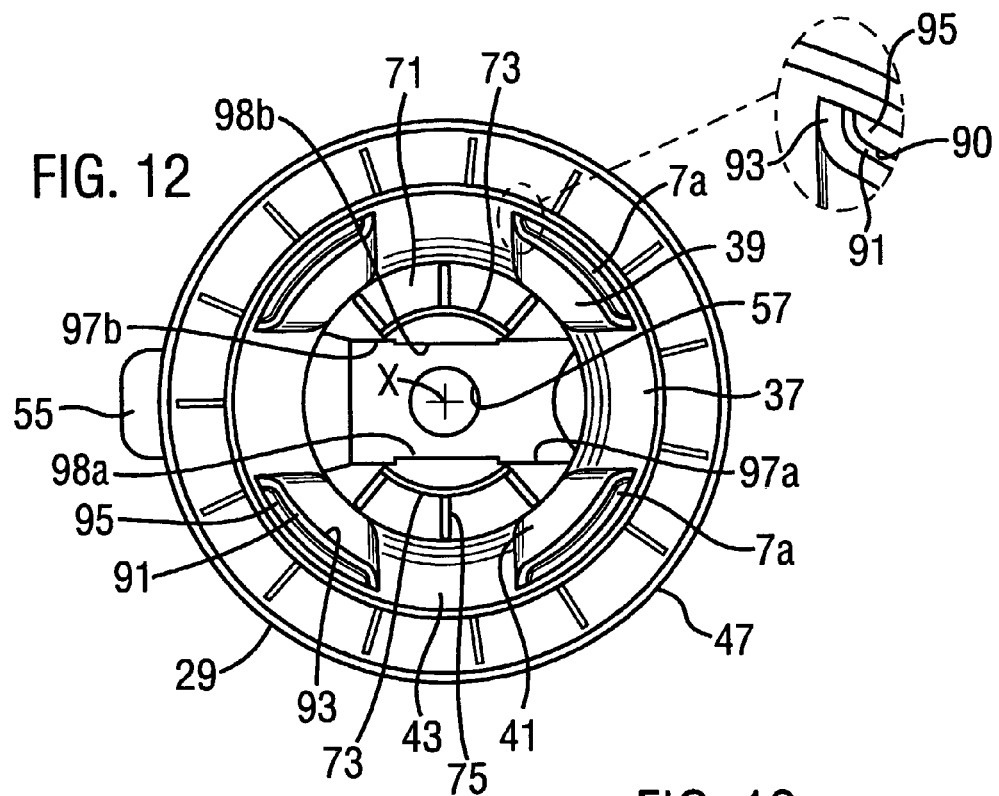
FIG. 12 is an underneath plan view of the container part.
Figure 13:
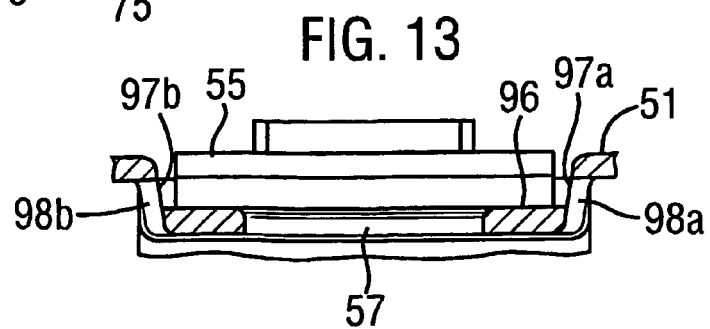
FIG. 13 is an enlargement of detail Y in FIG. 10.

Turning now to FIGS. 3, 9 and 12, from the inner surface 71 of the boss 51 extends a skirt formed by a pair of curved walls 73. The curved walls 73 are so constructed and arranged that they enclose the dispensing end of the bottle 100 having the rubber stopper 101 when the bottle 100 is held in the protective container 1. The curved walls 73 function as locators for the dispensing end of the bottle 100 as well as providing means for inhibiting lateral movement of the dispensing end in the protective container 1. The curved walls 73 are each provided with reinforcing ribs 75 on the outer surfaces thereof. The reinforcing ribs 75 act to prevent the curved walls 73 from being forced apart by the dispensing end of the bottle 100 on droppage of the container 1 to such an extent that the dispensing end is able to free itself from capture by the curved walls 73 and impact the inner surface of the cavity defined in the container part 3 for the bottle 100.

Turning now to FIGS. 1, 3 and 8 to 10, it can be seen that the aperture 57 is located in a recess 96 of the cylindrical boss 51 which is exposed when the flap 55 is hinged from its closed position to the open position. As shown most clearly in FIGS. 9, 12 and 13, the recess 96 has opposed side walls 97a, 97b in each of which is provided a slot 98a, 98b adjacent the aperture 57. The purpose of the recess 96 and the slots 98a, 98b will become clear shortly hereinafter.

Figure 11:
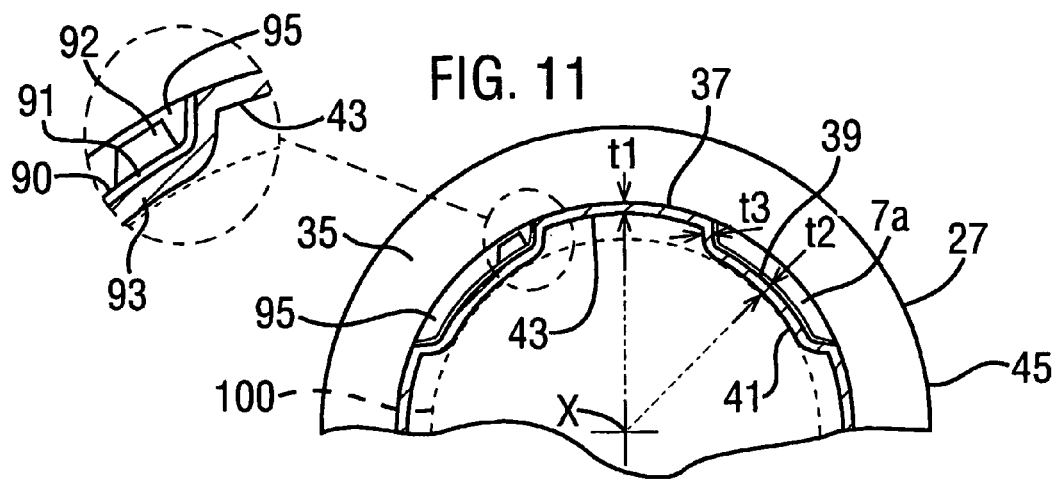
FIG. 11 is a fragmentary sectional view of the container part along line E—E in FIG. 10.

It can be seen from FIGS. 9 to 12 that the locking elements 7a of the container part 3 are formed at the ends of the depressions 39. The locking elements 7a are formed by a slot 91 which spaces apart a circumferential end surface 93 of the depression 39 from a rib 95. As shown in FIGS. 11 and 12, the rib 95 of each locking element 7a has an inner free surface 90 which is spaced radially outward from the end surface 93 of the depression 39. As will further be gathered from FIGS. 9 to 11, some, but not all, of the ribs 95 are provided with a stepped upper surface due to the presence of a tapered enlargement 92. Preferably, the tapered enlargements 92 are provided on a diametrically-opposed pair of ribs 95. Of course, all of the ribs 95 may be provided with a tapered enlargement 92, not just selected ones of the ribs.

As shown in FIG. 4, the locking elements 7b on the base part 5 take the form of equi-spaced, circumferentially-oriented ribs 80. Each rib 80 has a tapered leading portion 81, an enlarged trailing portion 83 and a recessed intermediate portion 85. The manner in which the locking elements 7a, 7b co-operate to lock the container and base parts 3, 5 together will be understood by reference to FIGS. 14A–C.

Firstly, the base part 5 is inserted into the lower open end 27 of the container part 3 with (i) the locking elements 7b positioned adjacent the ribs 37 between the locking elements 7a, and (ii) the rim 94 of the base part 5 abutting the end surfaces 93 of the locking elements 7a for registration purposes (FIG. 14A).

The base part 5 is then rotated relative to the container part 3 so that the leading portions 81 of the locking elements 7b enter the slots 91 of the locking elements 7a of the container part 3. As will be understood from FIG. 14B, the tapered profile of the leading portions 81 causes the circumferential end surfaces 93 and the associated ribs 95 to separate and/or the tapered leading portions 81 to compress so that the leading portions 81 pass beyond the enlargements 92. After the tapered leading portions 81 have passed the enlargements 92, the resilience of the material of the container and base parts 3, 5 results in the tapered leading portions 81 and/or the enlargements 92 being biased back to its original state whereby the enlargements 92 locate in the intermediate recessed portions 85 of the locking elements 7b, as shown in FIG. 14C. This causes the base part 5 to become locked to the container part 3 inasmuch as counter rotation of the base part 5 is inhibited by the engagement of the step surfaces of the enlargements 92 and the tapered leading portions 81.

Release of the container and base parts 3, 5 is effected by counter rotating the base part 5 relative to the container part 3 sufficiently forcefully to cause the tapered leading portions 81 of the ribs 80 of the base part 5 to pass back over the enlargements 92 of the ribs 95 of the container part 3.

It will be gathered from FIGS. 14A–C that the trailing portions 83 of the ribs 80 of the base part 5 act as a stop to limit the insertion of the ribs 80 into the slots 91. By the same token, the trailing portions 83 prevent counter rotation of the base part 5 when it is indexed with the container part 3 with the base part ribs 80 located in the container part ribs 37 prior to insertion into the slots 91 (see FIG. 14A). This guides the user to turn the base part 3 in the correct direction for locking and unlocking of the base part 5 from the container part 3.

It will, of course, be understood that other locking mechanisms for releasably locking the container and base parts 3, 5 can be used. As an example, other forms of snap fits, for instance based on interengaging complementary surfaces, such as stepped surfaces. The locking mechanism may also be actuated by movement of the base part 5 relative to the container part 3 other than by rotation or screwing.

An example of another form of locking mechanism is one in which the lower surface of the ribs 95 is left planar, or substantially planar. As the leading portions of the ribs 80 enter the associated slots 91, the tapered profile of the leading portions 81 causes the circumferential surfaces 93 and the associated ribs 95 to separate so that the leading portions can pass beyond the slots 91. The slots 91 then close behind the leading portions 81. In so doing, the ribs 95 become locked in the intermediate recessed portions 85 of the locking elements 7b, due to the steps formed between the intermediate portions 85 and the leading and trailing portions 81, 83 of the ribs 80, causing the base part 5 to become locked to the container part 3. Release of the container and base parts 3, 5 is effected by squeezing the container part 3 to open the slots 91 so that the direction of relative rotation of the base part 5 can be reversed.

In FIGS. 15 to 19 there is shown a nozzle accessory 150 for mounting on the upper end 29 of the protective container 1 for discharge of the contents of the bottle 100. The nozzle accessory has a central piercing part 151 and an outer connector part 153. The piercing and connector parts 151, 153 are preferably injection moulded from plastics materials.

The piercing part 151 has a longitudinal axis L and comprises a central body 154, a spike 155 projecting from a flange 156 of the body 154 in a first direction and an elongated extension 157 which extends in a second opposite direction from the body 154.

As shown in FIG. 16, the piercing part 151 is provided with first 159 and second 160 internal axial passageways. The first passageway 159 extends from an opening 161 in a tip 163 of the spike 155 to an opening 165 at the end of the extension 157. The second passageway 161, on the other hand, extends from an opening 167 in the tip 163 of the spike 155 into a blind bore 169 which extends laterally into the body 154 of the piercing part 151.

As further shown in FIG. 16, the extension 157 of the piercing part 151 tapers inwardly in the second direction and is provided with a series of serrations or barbs 171 on its outer surface to enable a tube 173 connected to an automatic or manual syringe or other dispensing device (not shown) to be connected to the extension 157 by an interference fit. The barbs 171 taper outwardly in the first direction to give the extension a sawtooth profile. The sawtooth profile enables the tube 173 to be pushed over the barbs 171 in the first direction for locating the tube 173 on the extension 157 but provides resistance against efforts to pull the tube 173 off the extension 157 in the second direction.

As will be understood from FIG. 15, an elastic or rubber bung 174 is mounted in the blind bore 169 in the central body 154 of the piercing part 151. The bung 174 has a short shaft 175 with a tip 179 and an enlarged head 181 for seating in a countersunk entrance 183 of the blind bore 169. A passageway 185 extends through the bung 174 from the head 181 to the tip 179 of the shaft 175. The tip 179 of the shaft 175 has a split 186 so that it can be opened and closed to open and close the passageway 185.

Turning to FIG. 16, the tip 163 of the spike 155 of the piercing part 151 has a notch 187 to provide a sharpened point 189 for piercing the rubber stopper 101 of the bottle 100, as will be understood shortly hereinafter. As can be seen, the notch 187 also results in the tip opening 167 to the second passageway 160 being located closer to the sharpened point 189 of the spike 155 than the tip opening 161 to the first passageway 159.

The connector part 153 of the nozzle accessory 150 has a hollow body 201 into which the piercing part 151 is able to be inserted to connect the piercing and connector parts 151, 153 together whilst allowing relative rotation therebetween about the longitudinal axis L. The body 201 has an annular skirt 203 which has external ribs 204 for a user to grip and a roof 205 across the skirt 203 at a trailing end 207 of the body 201.

An internal passageway 209 extends through the body 201 from a first opening 211 in a leading end 213 of the body 201 to a second opening 215 in the roof 205. The diameter of the second opening 215 in the roof 205 is smaller than the diameter of the first opening 211. In fact, the diameter of the second opening 215 is slightly less than the maximum diameter of the innermost barb 171 on the extension 157 whereby the extension 157 is able to be inserted through the roof 205, due to the tapered nature of the barbs 171, but not easily withdrawn. The diameter of the second opening 215 is also smaller than the dimensions of a trailing end face 217 of the body 154 of the piercing part 151. As shown in FIG. 16, this enables the connector part 153 to be held captive on the piercing part 151 with th roof 205 of the connector part 153 resting on the trailing end face 217 of the body 154 or the innermost barb 171 depending on the orientation of the nozzle accessory 150.

Preferably, the distance between the innermost barb 171 and the trailing end face 217 closely matches the thickness of the roof 205 of the connector part 153 so that, when the connector part 153 is mounted on the piercing part 151, relative axial displacement is limited.

The body 201 of the connector part 153 has an outwardly extending flange 219 at its leading end 213. The flange 219 has straight sides 221 which are connected by curved ends 223, as shown in FIG. 18. The spacing between the straight sides 221 corresponds to the spacing between the side walls 97a, 97b of the recess 96 in the boss 51 of the protective container 1. Thus, the connector part 153 can be indexed in the recess 96 through the complementary sides 97a, 97b, 221.

For operation of the container system 200, the following steps are undertaken as a preliminary measure:

The nozzle accessory 150 is assembled by inserting the piercing part 151 into the connector part 153 and connecting a syringe tube 173, as shown in FIG. 16.

The bottle 100 is inserted into the container part 3 of the protective container 1 so that the dispensing end thereof is located by the curved walls 73 underneath the cylindrical boss 51 with the rubber stopper 101 aligned with the aperture 57.

The base part 5 is secured to the container part 3 through the complementary locking features 7a, 7b, as shown in FIGS. 14A–C.

The flap 55 on the protective container 1 is then moved to its open position to reveal the aperture 57 and the rubber stopper 101 of the bottle 100 held in the protective container 1. The nozzle accessory 150 is then moved towards the upper end 29 of the protective container 1 to push the spike 155 through the aperture 57 and into the rubber stopper 101 of the bottle 100. As the tip opening 167 to the second passageway 160 is located closest to the sharpened point 189 of the spike 155, the second passageway 160 comes into fluid communication with the interior of the bottle 100 before the first passageway 159. This allows the bottle 100 to be vented, if need be, through the second passageway 160 and the associated bung 174. Further introduction of the spike 155 into the rubber stopper 101 of the bottle 100 results in the tip opening 161 to the first passageway 159 being put in fluid communication with the interior of the bottle 100.

The spike 155 of the piercing part 151 is inserted into the rubber stopper 101 of the bottle 100 until the flange 156 of the piercing part 151 contacts the rubber stopper 101 and the connector part 153 indexes in the recess 96 of the boss 51 by the flange 219 seating in the recess 96 with the respective sides 97a, 97b, 221 aligned. This indexed position is shown in FIG. 19A.

As shown in FIG. 19B, the connector part 153 is then rotated relative to the piercing part 151 from the indexed position in the recess 96 until the curved ends 223 of the flange 219 are inserted into the slots 98a, 98b in the side walls 97a, 97b of the recess 96. When the curved ends 223 of the flange 219 of the connector part 153 have been inserted into the slots 98a, 98b, the nozzle accessory 150 is fixedly secured to the protective container 1. However, the nozzle accessory 150 is able to be easily released from the protective container 1 by rotating the connector part 153 relative to the piercing part 151 to bring it back to its indexed position.

Once the nozzle accessory 150 has been secured to the protective container 1, the protective container 1 is hung by its fixed hanger 17 and the contents of the bottle 100 are able to be discharged through the first passageway 159 to the syringe or other dispensing device via the tube 173.

Typically, a vacuum builds up in the bottle 100 during dispensing as the contents are discharged through the nozzle accessory 150. The second passageway 160 with associated bung 174 provides a vent for the bottle 100 allowing easy evacuation of the product from the bottle 100 and avoids a vacuum build-up which makes injection inaccurate, slow and difficult. This would also be the case for other rigid containers. Such a vent system, however, would not be required if the bottle 100 were of a collapsible or pillow-pack type.

In FIGS. 20 to 25 of the drawings there is shown a protective container 1' according to an alternative embodiment of the present invention. The protective container 1' is identical to the protective container 1 of the container system 200 in all respects other than as follows.

Firstly, as shown in FIGS. 20 to 24 the central part of the channel 13' in the outer seating surface 9' of the base part 5' is formed as a ramp 15' on the apex of which is hinged a hanger 17' for hanging the protective container 1' in an inverted position. The hanger 17' is movable between a deployed position, in which it stands upright for an aperture 20' in the hanger to be accessible for hanging the protective container 1', and a retracted position, in which it is releasably secured in the channel 13' by catches 21'. In this way, the hanger 17' does not interfere with the base part 5' being used as a seat for the protective container 1'.

Turning to FIG. 23, when the base part 5' is viewed from underneath it can be seen that the protrusions 11a', 11b' are hollow. In this way, the bottom of the bottle 100 sits on the inner surface 23' of the channel 13', not the inner surfaces 25a', 25b' of the protrusions 11a', 11b'. The reason for this is as for the previously described protective container 1, namely avoiding impact forces being transmitted to the bottle 100 if the protective container 1' is dropped on its base part 5'. Thus, the likelihood of breakage of the bottle 100 is reduced compared to the case when using protective containers in the prior art. In fact, testing under National Safe Transit Association (NSTA) guidelines for packages weighing under 45.36 kg (100 lb) has shown that the protective container 1' provides better protection than prior art containers when dropped by a drop tester onto a concrete surface on its base part 5' from a height of 0.762 m (30 in). That is to say, compared to prior art containers, the protective container 1 more often (i) keeps the vial free from damage, and (ii) retains its integrity so as to still reasonably provide further protection for the bottle 100.

Secondly, the protective container 1' is not constructed to accept the nozzle accessory 150 of the container system 200 of FIGS. 1 to 19 inasmuch as slots are not provided in the side walls 97a', 97b' of the recess 96' of the boss 51' at the upper end 29' of the container part 3'. In this embodiment, a dose of the fluid medicament in the bottle 100 housed in the protective container 1' may be withdrawn by inserting a needle of a syringe (not shown) through the rubber stopper 101 via the aperture 57' in the recess 96' of the boss 51'.

Thirdly, the flap 55' used to close the aperture 57' is secured in the closed position through an interference fit between a plug 63' and the aperture 57'. Of course, other forms of securing mechanism for securing the flap 55' in the closed position can be employed in the practice of the invention.

It will be appreciated that the new features exhibited in the protective container 1' of FIGS. 20 to 25 are not mutually dependent on one another. Accordingly, these features can be 'pick-and-mixed' in the practice of the present invention. As an example, the base part 5 of the protective container 1 can be switched for the base part 5' of the alternative protective container 1' without any other changes being made. Conversely, slots may be provided in the side walls 97a', 97b' of the boss recess 96' of the alternative protective container 1' so that it can accept the nozzle accessory 150 without changing the plug 63' on the flap 55' or the base part 5'.

In addition to the NSTA tests referred to above, drop tests conducted on the protective containers 1; 1' at ambient temperature show that there is no bottle breakage after consecutive drops on the opposite ends 9, 29; 9', 29' and the side 31; 31' from a height of 1 m onto a rigid surface. The same results are also achieved at 5° C. Even when the protective container 1; 1' (but not the bottle 100) is at a temperature of −18° C., the bottle 100 only breaks in 20% of such drop tests.

The critical drop height (CDH) for each drop position has also been measured at ambient temperature and 5° C. The results are tabulated below.

| Temperature (° C.) | CDH Drop on Base Part (m) | CDH Drop on Upper End (m) | CDH Drop on Side (m) |
|---|---|---|---|
| Ambient | 2.1 | 2.2 | 2.0 |
| 5 | 2.2 | 2.2 | 1.7 |

By "critical drop height" is meant that drop height above which the protective container 1; 1' cannot be expected to protect the bottle 100 from breakage.

As demonstrated, the exemplary protective containers 1; 1' of the present invention provide significant bottle protection.

Referring now to FIGS. 26A and 26B, an information-containing label 101 is shown affixed to the boss 51' of the alternative protective container 1' of FIGS. 20 to 25 when the flap 55' is in its closed position. The label 101 may, for instance, contain instructions on how to latch the flap 55' in its open position to allow insertion of a syringe needle into the rubber stopper 101 of the bottle 100. The label would have weakened or tear lines (e.g. perforations) in registration with the edges of the flap 55' so as to divide the label 101 into a central section 101a on the flap 55' and a pair of diametrically opposed part-spherical side sections 101b on the boss 51'.

As will be understood from FIG. 26B, the result of this is that on first opening of the flap 55' the central section 101a of the label 101 is separated from the part-spherical side sections 101b. When the flap 55' is closed, however, the central and side label sections 101a, 101b come back together to reconstitute the label 101 for reading on next administration of a dose of the medicament in the bottle 100. This avoids placing a label on the cylindrical body 31' of the container part 3' which would impede viewing of a label on the bottle 100.

As will be understood by the skilled reader in the art, the use of an information-containing label 101 is not restricted to the alternative protective container 1' of FIGS. 20 to 25, but has equal application for use on the protective container 1 shown in FIGS. 1 to 19. The label 101 in this instance may contain instructions on how to attach the nozzle accessory 150 to the protective container 1, for example.

The protective containers as herein described have several advantages over the protective containers hitherto used for containing fragile, e.g. glass, receptacles of medicament, an inexhaustive list of such advantages being:
1. Improved impact protection for the receptacle.
2. Integrated means for hanging the container in an inverted position so as to assist the user in inserting a nozzle or syringe into the bottle.
3. A latching mechanism for latching the flap in a position which does not impede the user when inserting a nozzle or needle into the bottle.
4. An ergonomic profile to aid gripping of the protective container.

It will be understood by the skilled reader that the present invention is not limited to the exemplary embodiments herein described and that many variations and modifications may be made within the scope of the appended claims. For example, other flexible or resilient materials beside polypropylene (plastics and otherwise) may be used for the protective container. In addition, the collars of the protective container may be discontinuous, e.g. in the form of a broken ring of discrete beads. Alternately, the collars may be dispensed with and the panel spacing on the side of the container part selected such that the protective container will always land on one of the ribs in a side-on impact. Furthermore, the base part may be permanently connected to the container part and movable between open and closed positions to allow insertion and withdrawal of the bottle, e.g. through a hinged connection.

It will also be understood by the skilled reader that the present invention is not restricted to the provision of a protective container for a liquid medicament such as Micotil®. The protective container of the invention has application for other receptacles and contents to be dispensed, whether in liquid form, powder form, or some other form, as well as application for storage and transportation of fragile articles in general, e.g. ceramic or glass structures.

It will yet further be understood by the skilled reader that the use of reference numerals in the appended claims is purely for illustration and not meant to be limiting on the scope of the claims.

What is claimed is:

1. A protective container for housing a fragile article comprising:
a container portion and a base portion, said container portion comprising: an upper end, a lower end, and a generally cylindrical side surface extending lengthwise along a longitudinal axis from said upper end to said lower end, said cylindrical side surface forming a cavity therein for housing the fragile article, wherein said cylindrical side surface comprises an inner wall surface and an outer wall surface, said inner wall surface comprising a configuration of inner wall ribs and inner wall depressions, said outer wall surface comprising a configuration of outer wall ribs and outer wall depressions, wherein said outer wall depressions correspond with said inner wall ribs and said outer wall ribs correspond with said inner wall depressions, and wherein said container portion further comprises an upper end collar and a lower end collar, both extending laterally beyond the outer wall ribs; wherein each collar is adapted to absorb impact energy in the event of an impact thereon to protect the fragile article from breakage; and wherein said base portion is releasably securable to said container portion.

2. The protective container of claim 1 wherein said inner wall ribs of said container portion contact and position the fragile article within said cavity.

3. The protective container of claim 1 wherein said inner wall surface ribs and depressions and said outer wall surface ribs and depressions extend parallel to said longitudinal axis.

4. The protective container of claim 1 wherein said base portion further comprises a locking element for engagement with a corresponding locking element on said container portion.

5. The protective container of claim 1 wherein said base portion further comprises an outer seating surface having a raised perimeter wherein said seating surface is adapted to absorb impact energy sufficient to protect the fragile article from breakage.

6. The protective container of claim 1 wherein said container portion further comprises a boss at an upper end and curved walls extending downward from an inner surface of said boss to locate and enclose a portion of a fragile article within said cavity.

7. The protective container of claim 6 wherein said container portion further comprises an aperture in said boss for access to the fragile article housed within said cavity.

8. The protective container of claim 1 further comprising a means for hanging said container.

9. The protective container of claim 8 wherein said means for hanging comprises two protrusions separated by a central channel on an exterior surface of said base extending along said longitudinal axis and a fixed hanger element connected to said protrusions and positioned in the central channel.

10. The protective container of claim 8 wherein said means for hanging comprises two protrusions separated by a central channel on an exterior surface of said base extending along said longitudinal axis and a releasably secured hanger element moveable between a deployed position and a retracted position in respect to said base and positioned in the central channel.

11. A protective container for housing a fragile article comprising:
- a container portion and a base portion, said container portion comprising: an upper end, a lower end, and a generally cylindrical side surface extending lengthwise along a longitudinal axis from said upper end to said lower end, said cylindrical side surface forming a cavity therein for housing the fragile article, wherein said cylindrical side surface comprises an inner wall surface and an outer wall surface, said inner wall surface comprising a configuration of inner wall ribs and inner wall depressions, said outer wall surface comprising a configuration of outer wall ribs and outer wall depressions, wherein said outer wall depressions correspond with said inner wall ribs and said outer wall ribs correspond with said inner wall depressions; and wherein said container portion further comprises a boss at an upper end and curved walls extending downward from an inner surface of said boss to locate and enclose a portion of a fragile article within said cavity and an aperture in said boss for access to the fragile article housed within said cavity, and a flap secured to said container portion and movable between a closed position to prevent access to said aperture and an open position to permit access to said aperture; and a latch mechanism for securing said flap in said open or closed position; and wherein said base portion is releasably securable to said container portion.

12. A protective container system housing a fragile article comprising:
- a container portion and a base portion, said container portion comprising: an upper end, a lower end, and a generally cylindrical side surface extending lengthwise along a longitudinal axis from said upper end to said lower end, said cylindrical side surface forming a cavity therein for housing the fragile article, wherein said cylindrical side surface comprises an inner wall surface and an outer wall surface, said inner wall surface comprising a configuration of inner wall ribs and inner wall depressions, said outer wall surface comprising a configuration of outer wall ribs and outer wall depressions, wherein said outer wall depressions correspond with said inner wall ribs and said outer wall ribs correspond with said inner wall depressions; and wherein said container portion further comprises an upper end collar and a lower end collar, both extending laterally beyond the outer wall ribs; wherein each collar is adapted to absorb impact energy in the event of an impact thereon to protect the fragile article from breakage; and wherein said base portion is releasably securable to said container portion; and
- a nozzle accessory for mounting on an upper end of said protective container comprising a central piercing part and an outer connector part, said contral piercing part having a longitudinal axis comprising along said axis a spike projecting from a flange of a central body and an elongated extension having serrations on its outer surface wherein the central body is housed within the outer connector part and said outer connector part is adapted to allow rotation about the longitudinal axis of said central piercing part for releasably connecting said nozzle accessory to said protective container.

13. The protective container system of claim 12 wherein said outer connector part of said nozzle accessory further comprises an outwardly extending flange having straight sides and curved ends.

14. The protective container system of claim 13 wherein said straight sides of said outwardly extending flange seats said nozzle accessory in a recess at an upper end of the container portion of said system.

15. The protective container system of claim 14 further comprising slots in side walls of said recess adapted to receive the curved ends of said flange of the outer connector part.

16. The protective container system of claim 15 wherein said nozzle accessory is connected to said protective container by engagement of said curved ends of said outwardly extending flange of the outer connector part into said slots in side walls of the recess at an upper end of the container portion of said system.

17. A package comprising a protective container for housing a fragile article and a fragile article wherein:
- the protective container comprises a container portion and a base portion, said container portion comprising: an upper end, a lower end, and a generally cylindrical side surface extending lengthwise along a longitudinal axis from said upper end to said lower end, said cylindrical side surface forming a cavity therein for housing the fragile article, wherein said cylindrical side surface comprises an inner wall surface and an outer wall surface, said inner wall surface comprising a configuration of inner wall ribs and inner wall depressions, said outer wall surface comprising a configuration of outer wall ribs and outer wall depressions, wherein said outer wall depressions correspond with said inner wall ribs and said outer wall ribs correspond with said inner wall depressions; wherein said container portion further comprises an upper end collar and a lower end collar, both extending laterally beyond the outer wall ribs, wherein each collar is adapted to absorb impact energy in the event of an impact thereon to protect the fragile article from breakage; and wherein said base portion is releasably securable to said container portion.

18. The package of claim 17 wherein said fragile article is a glass bottle, vial or ampoule.

19. The package of claim 18 wherein said fragile article contains a medicament.

20. The package of claim 19 wherein said medicament is a fluid.

21. The package of claim 20 wherein said fluid medicament comprises tilmicosin or a pharmaceutically acceptable salt thereof.

22. A package comprising a protective container for housing a fragile article and a fragile article wherein:
- the protective container comprises a container portion and a base portion, said container portion comprising: an upper end, a lower end, and a generally cylindrical side surface extending lengthwise along a longitudinal axis from said upper end to said lower end, said cylindrical side surface forming a cavity therein for housing the fragile article, wherein said cylindrical side surface comprises an inner wall surface and an outer wall surface, said inner wall surface comprising a configuration of inner wall ribs and inner wall depressions, said outer wall surface comprising a configuration of outer wall ribs and outer wall depressions, wherein said outer wall depressions correspond with said inner wall ribs and said outer wall ribs correspond with said inner wall depressions; wherein said container portion further comprises an upper end collar and a lower end collar, both extending laterally beyond the outer wall ribs, wherein each collar is adapted to absorb impact energy in the event of an impact thereon to protect the fragile article from breakage; and wherein said base portion is releasably securable to said container portion; and the fragile article is a glass bottle, vial or ampoule housed in said cavity.

23. The package of claim 22 wherein said fragile article contains a medicament.

24. The package of claim 23 wherein said medicament is a fluid.

25. The package of claim 24 wherein said fluid medicament comprises tilmicosin or a pharmaceutically acceptable salt thereof.

* * * * *